United States Patent
Li et al.

(10) Patent No.: US 6,194,557 B1
(45) Date of Patent: Feb. 27, 2001

(54) NUCLEIC ACID MOLECULES ENCODING BAP-1 PROTEINS

(75) Inventors: Shengfeng Li, Belmont; David R. Phillips, San Mateo, both of CA (US)

(73) Assignee: Cor Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 08/753,038

(22) Filed: Nov. 18, 1996

(51) Int. Cl.[7] ............................. C12N 15/12; C12N 1/21; C12N 5/10; C12P 21/02
(52) U.S. Cl. ..................... 536/23.5; 536/23.1; 435/69.1; 435/71.1; 435/71.2; 435/252.3; 435/325; 435/455; 435/471
(58) Field of Search ..................... 536/23.5; 435/69.1, 435/243, 320.1, 325

(56) References Cited

U.S. PATENT DOCUMENTS

| | | |
|---|---|---|
| 5,192,746 | 3/1993 | Lobl et al. . |
| 5,260,277 | 11/1993 | McKenzie . |
| 5,580,979 | 12/1996 | Bachovchin . |

FOREIGN PATENT DOCUMENTS

WO 96 15145  5/1996 (WO) .

OTHER PUBLICATIONS

G. Marguerie et al., "Platelet Alpha–IIB–Beta–3: A Pharmacological Integrin As a Target to Design New Molecules with Antithrombotic Activity," *J. of Experimental and Clinical Hematology*, vol. 35, No. 3, pp. 253–254 (1993).

M.J.S. Dyer et al., "Identification of Novel Ring Finger Genes that Interact with BCL7A," Abstracts of Papers Presented at the Annual Scientific Mtg., of the British Soc. For Haematology, p. 10, Abstract No. 32 (Apr. 14–17, 1997).

J. Schoorlemmer et al., Ring1A is a Transcriptional Repressor that Interacts with the Polycomb–M33 Protein and is Expressed at Rhombomere Boundaries in the Mouse Hindbrain, The EMBO Journal, vol. 16, No. 19, pp. 5930–5942 (Oct. 1, 1997).

Argraves, W. S., et al., Fibulin, a Novel Protein that Interacts with the Fibronectin Receptor β Subunit Cytoplasmic Domain, Cell, vol. 58, pp. 623–629 (1989).

Bartfeld, N.S., et al., The $\alpha_v\beta_3$ Integrin Associates with a 190–kDa Protein That is Phosphorylated on Tyrosine in Response to Platelet–derived Growth Factor, Journal of Biological Chemistry, vol. 268, pp. 17270–17276 (1993).

Blystone, Scott D., et al., Inducible Tyrosine Phosphorylationof the $\beta_3$ Integrin Requires the $\alpha_v$ Integrin Cytoplasmic Tail, Journal of Biological Chemistry, pp. 31458–31462 (1996).

Califf, Dr. Robert M. et al., Use of a Monoclonal Antibody Directed Against the Platelet Glycoprotein IIb/IIIa Receptor in High–Risk Coronary Angioplasty, New England Journal of Medicine, vol. 330, pp. 956–961 (1994).

Chen, Y.P., et al., "Inside–out" Signal Transduction Inhibited by Isolated Integrin Cytoplasmic Domains, Journal of Biological Chemistry, vol. 269, pp. 18307–18310 (1994).

Clark et al., Integrins and Signal Transduction Pathways: The Road Taken, Science, vol. 268, pp. 233–239 (1995).

Dedhar S., et al., Integrin cytoplasmic interactions and bidirectional transmembrane signaling, Current Opinion in Cell Biology, vol. 8, pp. 657–669 (1996).

Diamond, Michael S., et al., The Dynamic Regulation of Integrin Adhesiveness, Current Biology, vol. 4, pp. 506–517 (1994).

Faull, Randall J., et al., Dynamic Regulation of Integrins, Stem Cells, vol. 13, pp. 38–46 (1995).

Filardo, Edward J., et al., Requirement of the NPXY Motif in the Integrin β3 Subunit Cytoplasmic Tail for Melanoma Cell Migration in Vitro and In Vivo, Journal of Cell Biology, vol. 130, No. 2, pp. 441–450 (1995).

Findik, Duygu, et al., Platelet Membrane Glycoproteins IIb and IIIa are Substrates of Purified $pp60^{c-src}$ Protein Tyrosine Kinase, FEBS, vol. 262, No. 1, pp. 1–4 (1990).

Fitzgerald, Laurence A., et al., Protein Sequence of Endothelial Glycoprotein IIIa Derived from a cDNA Clone, Journal of Biological Chemistry, vol. 262, No. 9, pp. 3936–3939 (1987).

Fox, Joan E.B., et al., On the Role of the Platelet Membrane Skeleton in Mediating Signal Transduction, Journal of Biological Chemistry, vol. 268, pp. 25973–25984 (1993).

Ginsberg, M.H., et al., Platelet Integrins, Thrombosis and Haemostasis, vol. 70, pp. 87–93 (1993).

Ginsberg, M.H., et al., Inside–out Integrin Signaling, Current Opinion Cell Biol., vol. 4, pp. 766–771 (1992).

Grinblat, Yevgenya, et al., Functions of the Cytoplasmic Domain of the $B_{PS}$ Integrin Subumit During Drosophila Development, Development, vol. 120, pp. 91–102 (1994).

Haas, Thomas A., et al., The Cytoplasmic Domains of Platelet Glycoprotein IIb–IIIa ($\alpha_{IIb}\beta_3$) Interact in a Cation Dependent Manner, Journal of the International Society on Thrombosis and Haemostasis, vol. 73, No. 6, p. 1190 (1995).

Haimovich et al., Tyrosine Phosphorylation and Cytoskeletal Reorganization in Platelets Are Triggered by Interaction of Integrin Receptors with Their Immobilized Ligands, Journal of Biological Chemistry, vol. 268, pp. 15868–15877 (1993).

(List continued on next page.)

Primary Examiner—Christina Y. Chan
Assistant Examiner—Phillip Gambel
(74) Attorney, Agent, or Firm—Morgan, Lewis & Bockius LLP

(57) ABSTRACT

The present invention provides the amino acid and nucleotide sequence of a protein that binds to β3 integrins, αIIb and Src kinase and is involved in integrin mediated signaling. Based on this disclosure, the present invention provides methods for identifying agents that block integrin mediated signaling, methods of using agents that block integrin mediated signaling to modulate biological and pathological processes, and agents that block integrin mediated signaling.

16 Claims, 6 Drawing Sheets

OTHER PUBLICATIONS

Hannigan, Gregory E., et al., Regulation of Cell Adhesion and Anchorage–dependent Growth by a New $\beta_1$–Integrin–Linked Protein Kinase, Nature, vol. 379, pp. 91–96 (1996).

Hayashi, Yokichi, et al., Expression and Function of Chicken Integrin $\beta1$ Subunit and its Cytoplasmic Domain Mutants in Mouse NIH 3T3 Cells, Journal of Cell Biology, vol. 110, pp. 175–184 (1990).

Hibbs, Margaret L., et al., The Cytoplasmic Domain of the Integrin Lymphocyte Function–associated Antigen 1 $\beta$ Subunit: Sites Required for Binding to Intercellular Adhesion Molecule 1 and the Phorbol Ester–stimulated Phosphorylation Site, J. Exp. Med., vol. 174, pp. 1227–1238 (1991).

Hillery, Cheryl, et al., Phosphorylation of Human Platelet Glycoprotein IIIa (GPIIIa), Journal of Biological Chemistry, vo. 266, No. 22, pp. 14663–14669 (1991).

Hirsch, E., et al., Impaired migration but not differentiation of haematopoietic stem cells in the absence of $\beta_1$ integrins, Nature, vol. 380, pp. 171–175 (1996).

Hirst, Roger, et al., Phosphorylation of the Fibronectin Receptor Complex in Cells Transformed by Oncogenes that Encode Tyrosine Kinase, Proc. Natl. Acad. Sci. USA, vol. 83, pp. 6470–6474 (1986).

Horwitz, Alan, et al., Interaction of Plasma Membrane Fibronectin Receptor with Talin—a Transmembrane Linkage, Nature, vol. 320, pp. 531–533 (1986).

Hsu, Hailing, et al., TRADD–TRAF2 and TRADD–FADD Interactions Define Two Distinct TNF Receptor 1 Signal Transduction Pathways, Cell, vol. 84, pp. 299–308 (1996).

Huang, M.M., et al., Adhesive Ligand Binding to Integrin $\alpha_{IIb}\beta_3$ Stimulates Tyrosine Phosphorylation of Novel Protein Substrates before Phosphorylation of pp125$^{FAK}$, Journal of Cell Biology, vol. 122, pp. 473–483 (1993).

Hughes, P.E., et al., The Conserved Membrane–proximal Region of an Integrin Cytoplasmic Domain Specifies Ligand Binding Affinity, Journal of Biological Chemistry, vol. 270, pp. 12411–12417 (1995).

Huttenlocher, A., et al., Modulation of Cell Migration by Integrain–mediated Cytoskeletal Linkages and Ligand–binding Affinity, Journal of Cell Biology, vol. 134, pp. 1551–1562 (1996).

Hynes, R.O., Integrins: Versatility, Modulation, and Signaling in Cell Adhesion, Cell, vol. 69, pp. 11–25 (1992).

Johansson, Mats W., et al., Altered Localization and Cytoplasmic Domain–binding Properties of Tyrosine–phosphorylated $\beta_1$ Integrin, Journal of Cell Biology, vol. 126, pp. 1299–1309 (1994).

Juliano, R.L. and Haskill, S., Signal Transduction from the Extracellular Matrix, Journal of Cell Biology, vol. 120, pp. 577–585 (1993).

Kieffer, Nelly., et al., Adhesive Properties of the $\beta_3$ Integrins: Comparison of GP IIB–IIIa and the Vitronectin Receptor Individually Expressed in Human Melanoma Cells, Journal of Cell Biology, vol. 113, pp. 451–461 (1991).

Knezevic, I., et al., Direct Binding of the Platelet Integrin $\alpha_{IIb}\beta_3$ (GPIIb–IIIa) to Talin, Journal of Biological Chemistry, vol. 271, pp. 16416–16421 (1996).

Kolanus et al., $\alpha L\beta 2$ Integrin/LFA–1 Binding to ICAM–1 Induced by Cytohesin–1, a Cytoplasmic Regulatory Molecule, Cell, vol. 86, pp. 233–242 (1996).

LaFlamme, Susan E., et al., Single Subunit Chimeric Integrins as Mimics and Inhibitors of Endogenous Integrin Functions in Receptor Localization, Cell Spreading and Migration, and Matrix Assembly, Journal of Cell Biology, vol. 126, No. 5, pp. 1287–1298 (1994).

Lanza, F., et al., cDNA Cloning and Expression of Platelet p24/CD9, Journal of Biological Chemistry, vol. 266, pp. 10638–10645 (1991).

Lauffenburger, Douglas A., et al., Cell Migration: A Physically Integrated Molecular Process, Cell, vol. 84, pp. 359–369 (1996).

Law, Debbie A., et al. Outside–in Intgrin Signal Transduction, Journal of Biological Chemistry, vol. 271, pp. 10811–10815 (1996).

Lin, S., et al, Mapping of Actin Vinculin, and Integrin Binding Domains Suggests A Direct Role of Tensin in Actin–Membrane Association, Tuesday, Cytoskeleton–Membrane Interactions: Structure I, Abstract 2259, Annual Meeting of the 6th International Congress on Cell Biology, Dec. 9–11, 1996.

Lovering, Ruth, et al., Identification and Preliminary Characterization of a Protein Motif Related to the Zinc Finger, Proc. Natl. Acad. Sci. USA, vol. 90, pp. 2112–2116 (1993).

Lukashev, Matvey E., et al., Disruption of Integrin Function and Induction of Tyrosine Phosphorylation by the Autonomously Expressed $\beta_1$ Integrin Cytoplasmic Domain, Journal of Biological Chemistry, vol. 269, pp. 18311–18314 (1994).

Luscinskas et al., Integrins as Dynamic Regulators of Vascular Function, FASEB Journal, vol. 8, pp. 929–938 (1994).

Otey, Carol A., et al., Mapping of the $\alpha$–Actinin Binding Site within the $\beta_1$ Integrin Cytoplasmic Domain, vol. 268, Journal of Biol. Chem., pp. 21193–21197 (1993).

Otey, Carol A., et al. An Interaction between $\alpha$–Actinin and the $\beta_1$ Integrin Subunit In Vitro, Journal of Cell Biology, vol. 111, pp. 721–729 (1990).

O'Toole, Timothy E., et al., Affinity Modulation of the $\alpha_{IIb}\beta_3$ Integrin (platelet GPIIb–IIIa) is an Intrinsic property of the Receptor, Cell Regulation, vol. 1, pp. 883–893 (1990).

O'Toole, Timothy E., et al., Regulation of Integrin Affinity States through an NPXY Motif in the $\beta$ Subunit Cytoplasmic Domain, Journal of Biological Chemistry, vol. 270, No. 15, pp. 8553–8558 (1995).

Phillips, David R., et al., GPIIb–IIIa: The Responsive Integrin, Cell, vol. 65, pp. 359–362 (1991).

Phillips, David R., et al., The Platelet Membrane Glycoprotein IIB–IIIa Complex, Blood, vol. 71, pp. 831–843 (1988).

Parise, Leslie V., et al., Glycoprotein IIIa is Phosphorylated in Intact Human Platelets, Blood, vol. 75, No. 12, pp. 2363–2368 (1990).

Reddy, K.B., et al, Beta–Integrin Cytoplasmic Tails Interact with the Myosin–Cytoskeleton Linker Protein Skelemin, Tuesday, Cytoskeleton–Membrane Interactions: Function I, Abstract 2237, Annual Meeting of the 6th International Congress on Cell Biology, Dec. 9–11, 1996.

Reszka, Alfred A., et al., Identification of Amino Acid Sequences in the Integrin $\beta_1$ Cytoplasmic Domain Implicated in Cytoskeletal Association, Journal of Cell Biology, vol. 117, pp. 1321–1330 (1992).

Rothe, Mike, et al., A Novel Family of Putative Signal Transducers Associated with the Cytoplasmic Domain of the 75 kDa Tumor Necrosis Factor Receptor, Cell, vol. 78, pp. 681–692 (1994).

Ruoslahti, E., Integrins, Journal Clinical Investment, vol. 87, pp. 1–5 (1991).

Schaller, Michael D., pp125$^{FAK}$–Dependent Tyrosine Phosphorylation of Paxillin Creates a High–Affinity Binding Site for Crk, Molecular and Cell Biology, vol. 15, pp. 2635–2644 (1995).

Schaller, Michael D., et al., Focal Adhesion Kinase and Paxillin Bind to Peptides Mimicking β Integrin Cytoplasmic Domains, Journal of Cell Biology. pp. 1181–1187 (1995).

Schoenwaelder, Simone M., et al., Tyrosine Kinases Regulate the Cytoskeletal Attachment of Integrin $\alpha_{IIb}\beta_3$ (Platelet Gyycoprotein IIb/IIIa) and the Cellular Retraction of Fibrin Polymers, Journal of Biological Chemistry, vol. 269, pp. 32479–32487 (1994).

Sharma, Chander P., et al. Direct Interaction of Filamin (ABP–280) with the $\beta_2$–Integrin Subunit CD18[1], The Journal of Immunology, vol. 154. 3461–3470, (1995).

Shattil, Sanford J., et al., $\beta_3$–Endonexin, a Novel Polypeptide that Interacts Specifically with the Cytoplasmic Tail of the Integrin β3 Subunit, Journal of Cell Biology, vol. 131, No. 3, pp. 807–816 (1995).

Shattil, Stanford J., et al., Changes in the Platelet Membrane Glycoprotein IIb–IIIa Complex during Platelet Activation, Journal of Biological Chemistry, vol. 260, pp. 11107–11114 (1985).

Smyth, Susan S., et al., Regulation of Vascular Integrins, Blood, vol. 81, pp. 2827–2843 (1993).

Tamkun, John W., et al., Structure of Integrin, a Glycoprotein Involved in the Transmembrane Linkage between Fibronectin and Actin, Cell, vol. 46, pp. 271–282 (1986).

Tapley, Peter, et al., Integrins Isolated from Rous Sarcoma Virus–transformed Chicken Embryo Fibroblasts, Oncogene, vol. 4, pp. 325–333 (1989).

Tcheng, James E., et al., Multicenter, Randomized, Double–Blind, Placebo–Controlled Trial of the Platelet Integrin Glycoprotein IIb/IIIa Blocker Intergrin in Elective Coronary Intervention, Circulation, vol. 91, pp. 2151–2157 (1995).

Vuori, Kristen, et al., Association of Insulin Receptor Substrate–1 With Integrins, Science, vol. 266, pp. 1576–1578 (1994).

Walker, D.M., et al., Purification and Characterization of the 208 kDa Integrin Binding Protein, Tuesday, Cytoskeleton–Membrane Interactions: Function I, Abstract 2235, Annual Meeting of the 6th International Congress on Cell Biology, Dec. 9–11, 1996.

Weber, C., et al., Sequential Regulation of α4β1 and α5β1 Integrin Avidity by CC Chemokines in Monocytes: Implications for Transendothelial Chemotaxis, Journal of Cell Biology, vol. 134, pp. 1063–1073 (1996).

Xue–Yan, L., et al., Identification of a functionally important sequence in the cytoplasmic tail of integrin $\beta_3$ by using cell–permeable peptide analogs, Proc. Nat. Acad. Sci. USA, vol. 93, pp. 11819–11824 (1994).

Ylanne, J., et al., Distinct Functions of Integrin α and β Subunit Cytoplasmic Domains in Cell Spreading and Formation of Focal Adhesions, Journal of Cell Biology, vol. 122, No. 1, pp. 223–233 (1993).

Ylanne, J., et al., Mutation of the Cytoplasmic Domain of the Integrin $\beta_3$ Subunit, Journal of Biological Chemistry, vol. 270, pp. 9550–9557 (1995).

Lovering, R. et al. Proc. Natl. Acad. Sci. USA 90 (6): 2112–2116.

Hillier, L. et al. Wash U–Merck EST Project Genbank Accession No. 1264408 May 26, 1995.

Lovering, R. et al. Proc Natl. Acad. Sci. USA 90 (6) 2112–2116, Mar. 1993.*

Hillier, L. et al. Wash. U–Merck EST Project GenBank Accession No. 1264408 May 26, 1995.*

* cited by examiner

FIG. IA-1

```
GCCCCTCGCTCGCTCGCTCTCCTTCCCGCCCCCGCCAGGCGCCGAGCCGG
CTTCCCCTCAGTCTCTCATGAATATTGAGGCCCCTGTTGTATTTCCCGAGCT
CCATTGCGGAAGCTGAGGCTCGCCATATTGTGCGGCGGGCGGCGGTCCGCG
GCAGCTGATACCAGAGTCTTGCTCCGCGCGGCCAGCGGAGCCTGGGCTG
GGGCAGGAGCCGCAATGTCTCAGGCTGTGCAGACAAACGGAACTCAACCATT
AAGCAAAACATGGGAACTCAGTTTATATGAGTTACAACGAACACCTCAGGAG
GCAATAACAGATGGCTTAGAAATTGTGGTTTCACCTCGAAGTCTACACAGTG
AATTAATGTGCCCAATTGTTTGTTGAAGACTGGATATGTTGAAGAACACCATGACTACAAAG
GAGTGTTTACATCGTTTTGTGCAGACTGCATCATCACAGCCCTTAGAAGTGG
CAACAAAAGAATGTCCTACCTGTCGGAAAAACTAGTTTCCAAAGATCACTA
AGGCCAGACCCAAACTTTGATGCACTCAGCAAATTATCCAAGTCGTG
ATGAGTATGAAGCTCATCAAGAGAGTATTAGCCAGGATCAACAAGCACAA
TAATCAGCAAGCACTCAGTCACAGCATTGAGGAAGGACTGAAGATACAGGCC
ATGAACAGACTGCAGGAGGCAAGAAACAACAGATTGAAAATGAAATGTAGTGGA
GCAGAAGATAATGGTGACAGTTCACACTGCAGTAATGCATCCACACATAGCA
ATCAGGAAGCAGGCCCTAGTAACAATGGACCAAAACATCTGATGATTCTGG
GCTAGAGCTTGATAATAACAATGCAGCAATGCCTCATCCCACACTTATGGAT
GGTGCTAGTGAAATTGAATTAGTATTCAGGCGTGAGGTTAGCTTTAGAAGAA
AAGATGACAGTGCACAGACGAGATACATAAAGACTTCTGGTAACGCCACTGT
TGATCACTTATCCAAGTATCTGGCTGTGAGGTTAGCTTTAGAAGAACTTCGAA
GCAAAGGTGAATCAAACCAGATGAACCTTGATACAGCCAGTGAGAAGCAGT
ATACCATTTATATAGCAACAGCCAGTCACTGTATTAAATGGCTCT
TTTCTTTGGAATTGGTCAGTGAGAATACTGGAAAGTGAAACAACCCATGG
```

FIG. 1A-2

```
AACTTTATTATTACGGCACCTACAAAGGAGCACAAATGAGCCTTTAAAAACCAATT
CTGAGACTGAACTTTTATAGCCTATTTCTTTAATATTAAAGATGTACTGGC
ATTACTTTTATGGAGATCTTGGATATGTGTTCAATTTCTTCTTTCTGAGCCAGAC
TAGTTTACGCTATTCAAATCTTTCCCTTTATTTAAGATTTCCTTTTGGAAG
GGACTGCAATTATTCAGTATTTTTTCTTTAAAAATATATCTGAAGT
TCTGTGTTTTTTTTCCCCACAAAGTGTGTTCCACTGGTGTTCCACTGGCACCATTT
TGACCCAGGAATTTTCATAGTTTCTGTATTCTTATAAGATTCAGTGGCTGTC
CTTTCCTGCTCCCCTCAAAAGATTTTAGTCATACAGAATGTTAAATATTAT
GTATTCTGACTTTTTTTTCCCCCGGAGTCTGTATATTTATAGTTTCCTATAT
AAACTGTAGTATCTCATGAAGAACCAAGGCTCAAATTACTGTCCTTAAAA
ACAATTCTCATAGGATTATTCTTTCATGGTATTTCTTCCATATATCTCATT
TTAAAAAGAAGTTCTTATGAAACTTAGTGTCCATTGTCATGCAATGTTTTTT
TTTCCATTCTTTTCCCCTGTAATTTGGAATTTCTGGTCCTGGGAAGAATCAA
ACAAAATCTAAGTCTATGAGAACTTGGTTCATTGACATATTCTGCTGAAGA
AAGAAAAATTAAATTGGTAGTAAAATATAGTCTTCAAGTATACGTTTGAGAG
TGCTTTTTTTTGTATTAGTTCTGCTGTCCACTTCATTCCTGTATTATATGTGATG
TTTTTCCCCATTAAAATACCAGAGATAATGGAGATATTTGCACTTTAGCCTT
GATGAAAAGTACAAGATATGTTCAAAGCTTCCCTAATTTTTTTCTTATTGTA
GCCACATAAGTTTCAAGAATAACATGGCACACAGAACAATGGAAAAAGTTT
GTTCCATTGGAAAATTATATCATTTGGGTGCCACATCAGTTTATAAATTTG
GCGCTCTTTAATTACACTCTGTAGAAGGTTAATAGAGCTTGAGCCCTGCTTT
AATATGTAGTGAAAGATAATTCTGTAGAAAAACGTCAGCCAGTAGGGTAAAG
```

FIG. IA-3

```
TCATTCTACTGTTCTTAATTTTATATTGAGGAACAATATTGGGTGTTTGGGAG
CCAGAAAGCTTTGTTGACAGATCAGAAATAAGATTGACTTGGGTGTTATATTT
CATCTCTCCAGACTCTAGTATATTCCAACTTTATATCACAGTATTTAA
AAAGACATGTTGCATTGAGAAATTAACCCTAAAGGGTTTCAATAGGGTGT
AGACCTCCAGTACCTTTGTAACTAAAGTCTGTCTAGTCATTGTAAATATTTAT
CTGTCAGTTTTGACAGATTGGGGCCAGCTGTGTTTAAATCTTCAGCCCGG
TATGAAAACTTAAAGGTATATATTCAATTTTTACCATTTTATGGAAAATATT
TAAAATTTGTTTTTACAGGGTTTTTTTTTTTTTTTTTTGTAATCTGTGC
CATGAAATTTGAAAACCACCAAAAATCAAGGGAACTTTATATATTCAATTC
CTTTTCTGGTGTAAGTGTTTAAAGTTGTATAGATTATTAATGCATGCCCACTGAA
TATAACCCTGGTTTTGTGATAAAACTGCTTAGATTTGTTGATGACATTAGAT
TAGTAGTTGCATTAAATAACTAAATTCCCATTGTGATTAATTGAAATTTGTC
TTTAAGCAGAGAGTTATTTGTGACTATAAGCTTTGTGCTTAGAGAATGTATGT
GTTTTTATCTGTCAGTATGGGAGGAGGATATAAACTGCATCATTAGTGAAATTATT
GGTGTGTAATCCTTTGTGAAATATTCTAGTATTTGATAGGGTATTGAG
TGTATTTGTGTGTGTGGATGTGTGTTTGGGTACGGGAGAGGGGATGC
TATTGGCCATCACTACCAACCAGGGTTTCAAAAGTATACCTAAGTAATTT
CTTTTATCACTACCTCAACTGAGGAAGAAAAGGCTCACCACAAGTGGTGTGA
AGGCTTTGGGTACTTAGTTCTAAATTTTTTATGGTAACATATACATAGCCAC
ATTTACAGTTTAACCATTTTAAGGCATGTAATTCAGTGGGGTTAGGTACATT
CACAATGTTGTGTAATGATCACCGCCGTG
```

FIG. 1B

MSQAVQTNGTQPLSKTWELSLYELQRTPQEAITDGLEIVVSPRSLHSELMCPICLDM
LKNTMTTKECLHRFCADCIITALRSGNKECPTCRKKLVSKRSLRPDPNFDALISKIY
PSRDEYEAHQERVLARINKHNNQQALSHSIEEGLKIQAMNRLQRGKKQQIENGSG
AEDNGDSSHCSNASTHSNQEAGPSNKRTKTSDDSGLELDNNNAAMAIDPVMDGA
SEIELVFRPHPTLMEKDDSAQTRYIKTSGNATVDHLSKYLAVRLALEELRSKGESN
QMNLDTASEKQYTIYIATASGQFTVLNGSFSLELVSEKYWKVNKPMELYYAPTKE
HK

FIG. 2A

```
          10         20         30         40         50
 1234567890 1234567890 1234567890 1234567890 1234567890
 AGTGGAGCAG AAGATAATGG TGACAGCTCC CACTGTAGTA ACGCATCCAC   50
 ACACAGCAAC CAGGAAGCGG GCCCGAGTAA CAAACGGACC AAAACCTCTG  100
 ATGACTCTGG GCTTGATCTT GATAACAACA ATGCAGGAGT GGCGATTGAT  150
 CCAGTCATGG ACGGTGCCAG TGAGATTGAG TTAGTCTTCA GGCCCCATCC  200
 AACTCTTATG GAAAAGGACG ACAGCGCACA GACGAGATAC ATAAAGACTT  250
 CAGGCAATGC CACTGTTGAT CACTTATCCA AGTATCTGGC TGTGAGGTTA  300
 CCTTTAGAAG AACTTCGAAG CAAAGTGA                          328
```

FIG. 2B

SGAEDNGDSSHCSNASTHSNQEAGPSNKRTKTSDDSGLDLDNNNAGVAIDPVMD
GASEIELVFRPHPTLMEKDDSAQTRYIKTSGNATVDHLSKYLAVRLALEELRSKV

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 3467 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 226..1233

(xi) SEQUENCE DESCRIPTION: SEQ ID NO:1:

```
GCCCCTCGCT CGCTCGCTCC TTCCCGCCCT CCCCGCAGCG CCGGCCGAGC CGGCTTCCCC         60

TCAGTCTCTC ATGAATATTG AGCGGCCCCT GTTGTATTTC CCGAGCTCCA TTGCGGAAGC        120

TGAGGCTCGC CATATTGTGC GGCGGCGCCG GCGTCCGCGG CAGCTGATAC CAGAGTCTTG        180

CTCCGGCCGC GGCCAGCGGA GCCCTGGGCT GGGGCAGGAG CCGCA ATG TCT CAG           234
                                                 Met Ser Gln
                                                  1
```

```
GCT GTG CAG ACA AAC GGA ACT CAA CCA TTA AGC AAA ACA TGG GAA CTC    282
Ala Val Gln Thr Asn Gly Thr Gln Pro Leu Ser Lys Thr Trp Glu Leu
     5                  10                  15

AGT TTA TAT GAG TTA CAA CGA ACA CCT CAG GAG GCA ATA ACA GAT GGC    330
Ser Leu Tyr Glu Leu Gln Arg Thr Pro Gln Glu Ala Ile Thr Asp Gly
 20                  25                  30                  35

TTA GAA ATT GTG GTT TCA CCT CGA AGT CTA CAC AGT GAA TTA ATG TGC    378
Leu Glu Ile Val Val Ser Pro Arg Ser Leu His Ser Glu Leu Met Cys
             40                  45                  50

CCA ATT TGT TTG GAT ATG TTG AAG AAC ACC ATG ACT ACA AAG GAG TGT    426
Pro Ile Cys Leu Asp Met Leu Lys Asn Thr Met Thr Thr Lys Glu Cys
         55                  60                  65

TTA CAT CGT TTT TGT GCA GAC TGC ATC ATC ACA GCC CTT AGA AGT GGC    474
Leu His Arg Phe Cys Ala Asp Cys Ile Ile Thr Ala Leu Arg Ser Gly
     70                  75                  80

AAC AAA GAA TGT CCT ACC TGT CGG AAA AAA CTA GTT TCC AAA AGA TCA    522
Asn Lys Glu Cys Pro Thr Cys Arg Lys Lys Leu Val Ser Lys Arg Ser
 85                  90                  95

CTA AGG CCA GAC CCA AAC TTT GAT GCA CTC ATC AGC AAA ATT TAT CCA    570
Leu Arg Pro Asp Pro Asn Phe Asp Ala Leu Ile Ser Lys Ile Tyr Pro
100                 105                 110                 115

AGT CGT GAT GAG TAT GAA GCT CAT CAA GAG AGA GTA TTA GCC AGG ATC    618
Ser Arg Asp Glu Tyr Glu Ala His Gln Glu Arg Val Leu Ala Arg Ile
            120                 125                 130

AAC AAG CAC AAT AAT CAG CAA GCA CTC AGT CAC AGC ATT GAG GAA GGA    666
Asn Lys His Asn Asn Gln Gln Ala Leu Ser His Ser Ile Glu Glu Gly
        135                 140                 145

CTG AAG ATA CAG GCC ATG AAC AGA CTG CAG CGA GGC AAG AAA CAA CAG    714
Leu Lys Ile Gln Ala Met Asn Arg Leu Gln Arg Gly Lys Lys Gln Gln
    150                 155                 160

ATT GAA AAT GGT AGT GGA GCA GAA GAT AAT GGT GAC AGT TCA CAC TGC    762
Ile Glu Asn Gly Ser Gly Ala Glu Asp Asn Gly Asp Ser Ser His Cys
165                 170                 175

AGT AAT GCA TCC ACA CAT AGC AAT CAG GAA GCA GGC CCT AGT AAC AAA    810
Ser Asn Ala Ser Thr His Ser Asn Gln Glu Ala Gly Pro Ser Asn Lys
180                 185                 190                 195

CGG ACC AAA ACA TCT GAT GAT TCT GGG CTA GAG CTT GAT AAT AAC AAT    858
Arg Thr Lys Thr Ser Asp Asp Ser Gly Leu Glu Leu Asp Asn Asn Asn
            200                 205                 210

GCA GCA ATG GCA ATT GAT CCA GTA ATG GAT GGT GCT AGT GAA ATT GAA    906
Ala Ala Met Ala Ile Asp Pro Val Met Asp Gly Ala Ser Glu Ile Glu
        215                 220                 225

TTA GTA TTC AGG CCT CAT CCC ACA CTT ATG GAA AAA GAT GAC AGT GCA    954
Leu Val Phe Arg Pro His Pro Thr Leu Met Glu Lys Asp Asp Ser Ala
    230                 235                 240

CAG ACG AGA TAC ATA AAG ACT TCT GGT AAC GCC ACT GTT GAT CAC TTA   1002
Gln Thr Arg Tyr Ile Lys Thr Ser Gly Asn Ala Thr Val Asp His Leu
245                 250                 255

TCC AAG TAT CTG GCT GTG AGG TTA GCT TTA GAA GAA CTT CGA AGC AAA   1050
Ser Lys Tyr Leu Ala Val Arg Leu Ala Leu Glu Glu Leu Arg Ser Lys
260                 265                 270                 275

GGT GAA TCA AAC CAG ATG AAC CTT GAT ACA GCC AGT GAG AAG CAG TAT   1098
Gly Glu Ser Asn Gln Met Asn Leu Asp Thr Ala Ser Glu Lys Gln Tyr
            280                 285                 290

ACC ATT TAT ATA GCA ACA GCC AGT GGC CAG TTC ACT GTA TTA AAT GGC   1146
Thr Ile Tyr Ile Ala Thr Ala Ser Gly Gln Phe Thr Val Leu Asn Gly
        295                 300                 305

TCT TTT TCT TTG GAA TTG GTC AGT GAG AAA TAC TGG AAA GTG AAC AAA   1194
Ser Phe Ser Leu Glu Leu Val Ser Glu Lys Tyr Trp Lys Val Asn Lys
```

|  | 310 | 315 | 320 |  |
|---|---|---|---|---|

```
CCC ATG GAA CTT TAT TAC GCA CCT ACA AAG GAG CAC AAA TGAGCCTTTA        1243
Pro Met Glu Leu Tyr Tyr Ala Pro Thr Lys Glu His Lys
 325                 330                 335

AAAACCAATT CTGAGACTGA ACTTTTTTAT AGCCTATTTC TTTAATATTA AAGATGTACT     1303

GGCATTACTT TTATGGAGAT CTTGGATATG TTGTTCAATT TTCTTTCTGA GCCAGACTAG     1363

TTTACGCTAT TCAAATCTTT TCCCCTTTAT TTAAGATTTC CTTTTTGGAA GGGACTGCAA     1423

TTATTCAGTA TTTTTTTCTT TCCTTTAAAA AAATATATCT GAAGTTTCTT GTGTTTTTTT     1483

TTTTCCCCAC AAAGTGTGTT TCCACTTGGA GCACCATTTT GACCCAGGAA TTTTTCATAG     1543

TTTCTGTATT CTTATAAGAT TCAGTTGGCT GTCCTTTTCC TGCTCCCCTC AAAAGATTTT     1603

TAGTCATACA GAATGTTAAA TATTATGTAT TCTGACTTTT TTTTTCCCCC GGAGTCTTGT     1663

ATATTTATAG TTTTCCTATA TAAACTGTAG TATCTTCATG AAGAACCCAA GGCTCAAATT     1723

TACTGTCCTT AAAAACAATT CTCATAGGAT TATTCTTTTC ATGGTATTTT CTTCCATAAT     1783

ATCTCATTTT AAAAGAAGT  TCTTTATGAA ACTTAGTGTC CATTGTCATG CAATGTTTTT     1843

TTTTTCCATT CTTTTTCCCC TGTAATTTTG GAATTCTGG  TCCTGGGAAG AATCAAACAA     1903

AATCTTAAGT TCTATGAGAA CTTGGTTCAT TGACATATTC TGCTGAAGAA AGAAAAATTA     1963

AATTGGTAGT AAAATATAGT CTTCAAGTAT ACGTTTGAGA GTGCTTTTTT TTGTATTAGT     2023

TCTGCTGTCA CTTCATTTCC TGTATTATAT GTGATGTTTT TCCCCATTAA AATACCAGAG     2083

ATAATGGAGA TATTTTGCAC TTTAGCCTTG ATGAAAGTA  CAAGATATGT TCAAAGCTTC     2143

CCTAATTTTT TTCTTATTTG TAGCCACATA AGTTTCAAGA ATAACATGGC ACACAGAACA     2203

ATGGAAAAAA GTTTGTTTCC ATTGGAAAAT TATATCATTT TGGGTTGCCA CATCAGTTTA     2263

TAAATTTGGC GCTCTTTTAA TTACACTCTG TAGAAGGTTA ATAGAGCTTG AGCCCTGCTT     2323

TAATATGTAG TGAAAGATAA TTCTGTAGAA AAACGTCAGC CAGTAGGGTA AAGTCATTCT     2383

ACTGTTCTTA ATTTTTATAT TGAGGAACAA TATTGGGTGT TTGGGAGCCA GAAAGCTTTG     2443

TTGACAGATC AGAAATAAGA TTGACTTGGG TGTTATATTT CATCTCTCTC CAGACTCTAG     2503

GTATATTTCC AACTTTATAT ATCACAGTAT TTAAAAAGAC ATGTTTGCAT TGAGAAATTA     2563

ACCCTAAAGG GTTTTCAATA GGGTGTAGAC CTCCAGTACC TTTGTAACTA AAGTCTGTCT     2623

AGTCATTGTA AATATTTATC TGTCAGTTTT GACAGATTGG GGCCAGCTTG ATGTTTTAAA     2683

TCTTCAGCCC GGTATGAAAA CTTAAAGGTA TATATTCAAT TTTTTACCAT TTTATGGAAA     2743

ATATTTAAAA TTTGTTTTTA CAGGGTTTTT TTTTTTTTTT TTTTTTTTTT GTAATCTGTG     2803

CCATGAAATT TGAAACCAC  CAAAAATCAA GGGAACTTTT ATATATTCAA TTCCTTTTCT     2863

GGTGTAATGT TAAAGTTGTA TAGATTATTA ATGCATGCCC ACTGAATATA ACCCTGGTTT     2923

TGTGATAAAA CTGCTTAGAT TTTGTTGATG ACATTAGATT AGTAGTTGCA TTAAATAACT     2983

AAATTCCCAT TGTGATTAAT TGAAATTTTG TCTTTAAGCA GAGAGTTATT TGTGACTATA     3043

AGCTTTGTGC TTAGAGAATG TATGTGTTTT TATCTGTCAG TATGGGAGGA TATAAACTGC     3103

ATCATTAGTG AAATTATTGG TTGTGTAATC CTTTGTGAAA TATAATTCTA GGTATTTGAT     3163

AGGGTATTGA GTGTATTTTG TGTGTGTGTG GATGTGTGTT TTGGGGTACG GGGAGAGGCG     3223

ATGCTATTGG CCATCACTAC CAACCAGGGT TTCAAAAAGT ATATACCTAA GTAATTTCTT     3283

TTATCACTAC CTCAACTGAG GAAGAAAAGG CTCACCACAA GTGGTGTGAA GGCTTTGGGT     3343

ACTTAGTTCT AAATTTTTTT ATGGTAACAT ATACATAGCC ACATTTACAG TTTTAACCAT     3403

TTTAAGGCAT GTAATTCAGT GGGGTTAGGT ACATTCACAA TGTTGTGTAA TGATCACCGC     3463
```

CGTG                                                                     3467

(2) INFORMATION FOR SEQ ID NO:2:

(i) SEQUENCE CHARACTERISTICS:
        (A) LENGTH: 336 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Gln Ala Val Gln Thr Asn Gly Thr Gln Pro Leu Ser Lys Thr
 1               5                  10                  15

Trp Glu Leu Ser Leu Tyr Glu Leu Gln Arg Thr Pro Gln Glu Ala Ile
             20                  25                  30

Thr Asp Gly Leu Glu Ile Val Val Ser Pro Arg Ser Leu His Ser Glu
         35                  40                  45

Leu Met Cys Pro Ile Cys Leu Asp Met Leu Lys Asn Thr Met Thr Thr
     50                  55                  60

Lys Glu Cys Leu His Arg Phe Cys Ala Asp Cys Ile Ile Thr Ala Leu
 65                  70                  75                  80

Arg Ser Gly Asn Lys Glu Cys Pro Thr Cys Arg Lys Lys Leu Val Ser
                 85                  90                  95

Lys Arg Ser Leu Arg Pro Asp Pro Asn Phe Asp Ala Leu Ile Ser Lys
            100                 105                 110

Ile Tyr Pro Ser Arg Asp Glu Tyr Glu Ala His Gln Glu Arg Val Leu
        115                 120                 125

Ala Arg Ile Asn Lys His Asn Asn Gln Gln Ala Leu Ser His Ser Ile
130                 135                 140

Glu Glu Gly Leu Lys Ile Gln Ala Met Asn Arg Leu Gln Arg Gly Lys
145                 150                 155                 160

Lys Gln Gln Ile Glu Asn Gly Ser Gly Ala Glu Asp Asn Gly Asp Ser
                165                 170                 175

Ser His Cys Ser Asn Ala Ser Thr His Ser Asn Gln Glu Ala Gly Pro
            180                 185                 190

Ser Asn Lys Arg Thr Lys Thr Ser Asp Asp Ser Gly Leu Glu Leu Asp
        195                 200                 205

Asn Asn Asn Ala Ala Met Ala Ile Asp Pro Val Met Asp Gly Ala Ser
210                 215                 220

Glu Ile Glu Leu Val Phe Arg Pro His Pro Thr Leu Met Glu Lys Asp
225                 230                 235                 240

Asp Ser Ala Gln Thr Arg Tyr Ile Lys Thr Ser Gly Asn Ala Thr Val
                245                 250                 255

Asp His Leu Ser Lys Tyr Leu Ala Val Arg Leu Ala Leu Glu Glu Leu
            260                 265                 270

Arg Ser Lys Gly Glu Ser Asn Gln Met Asn Leu Asp Thr Ala Ser Glu
        275                 280                 285

Lys Gln Tyr Thr Ile Tyr Ile Ala Thr Ala Ser Gly Gln Phe Thr Val
290                 295                 300

Leu Asn Gly Ser Phe Ser Leu Glu Leu Val Ser Glu Lys Tyr Trp Lys
305                 310                 315                 320

Val Asn Lys Pro Met Glu Leu Tyr Tyr Ala Pro Thr Lys Glu His Lys
                325                 330                 335
```

(2) INFORMATION FOR SEQ ID NO:3:

(i) SEQUENCE CHARACTERISTICS:
        (A) LENGTH: 328 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..327

(xi) SEQUENCE DESCRIPTION: SEQ ID NO:3:

```
AGT GGA GCA GAA GAT AAT GGT GAC AGC TCC CAC TGT AGT AAC GCA TCC        48
Ser Gly Ala Glu Asp Asn Gly Asp Ser Ser His Cys Ser Asn Ala Ser
                340                 345                 350

ACA CAC AGC AAC CAG GAA GCG GGC CCG AGT AAC AAA CGG ACC AAA ACC        96
Thr His Ser Asn Gln Glu Ala Gly Pro Ser Asn Lys Arg Thr Lys Thr
            355                 360                 365

TCT GAT GAC TCT GGG CTT GAT CTT GAT AAC AAC AAT GCA GGA GTG GCG       144
Ser Asp Asp Ser Gly Leu Asp Leu Asp Asn Asn Asn Ala Gly Val Ala
        370                 375                 380

ATT GAT CCA GTC ATG GAC GGT GCC AGT GAG ATT GAG TTA GTC TTC AGG       192
Ile Asp Pro Val Met Asp Gly Ala Ser Glu Ile Glu Leu Val Phe Arg
385                 390                 395                 400

CCC CAT CCA ACT CTT ATG GAA AAG GAC GAC AGC GCA CAG ACG AGA TAC       240
Pro His Pro Thr Leu Met Glu Lys Asp Asp Ser Ala Gln Thr Arg Tyr
                405                 410                 415

ATA AAG ACT TCA GGC AAT GCC ACT GTT GAT CAC TTA TCC AAG TAT CTG       288
Ile Lys Thr Ser Gly Asn Ala Thr Val Asp His Leu Ser Lys Tyr Leu
            420                 425                 430

GCT GTG AGG TTA GCT TTA GAA GAA CTT CGA AGC AAA GTG A                 328
Ala Val Arg Leu Ala Leu Glu Glu Leu Arg Ser Lys Val
        435                 440                 445
```

(2) INFORMATION FOR SEQ ID NO:4:

(i) SEQUENCE CHARACTERISTICS:
        (A) LENGTH: 109 amino acids
        (B) TYPE: amino acid
        (D) TOPOLOGY: linear (ii) MOLECULE TYPE: protein (xi) SEQUENCE DESCRIPTION: SEQ ID NO:4:

```
Ser Gly Ala Glu Asp Asn Gly Asp Ser Ser His Cys Ser Asn Ala Ser
1               5                   10                  15

Thr His Ser Asn Gln Glu Ala Gly Pro Ser Asn Lys Arg Thr Lys Thr
            20                  25                  30

Ser Asp Asp Ser Gly Leu Asp Leu Asp Asn Asn Asn Ala Gly Val Ala
        35                  40                  45

Ile Asp Pro Val Met Asp Gly Ala Ser Glu Ile Glu Leu Val Phe Arg
50                  55                  60

Pro His Pro Thr Leu Met Glu Lys Asp Asp Ser Ala Gln Thr Arg Tyr
65                  70                  75                  80

Ile Lys Thr Ser Gly Asn Ala Thr Val Asp His Leu Ser Lys Tyr Leu
            85                  90                  95

Ala Val Arg Leu Ala Leu Glu Glu Leu Arg Ser Lys Val
            100                 105
```

(2) INFORMATION FOR SEQ ID NO:5:

(i) SEQUENCE CHARACTERISTICS:

```
        (A) LENGTH: 39 amino acids
        (B) TYPE: amino acid
        (C) STRANDEDNESS: single
        (D) TOPOLOGY: linear (xi) SEQUENCE DESCRIPTION: SEQ ID NO:5:

Cys Xaa Xaa Cys Xaa Xaa Xaa Xaa Xaa Xaa Xaa Xaa Xaa Xaa Glu
1               5                   10                  15

Cys Leu His Xaa Phe Cys Xaa Xaa Cys Xaa Xaa Xaa Xaa Xaa Xaa
            20                  25                  30

Xaa Xaa Xaa Xaa Cys Xaa Xaa
            35
```

NUCLEIC ACID MOLECULES ENCODING BAP-1 PROTEINS

FIELD OF THE INVENTION

The present invention relates to the field of integrin-mediated signaling, particularly signal transcduction mediated by β3 integrins such as αVβ3 and αIIbβ3. The invention relates specifically to the identification of a novel human gene, tentatively named Bap-1. Bap-1 encodes a protein, Bap-1, that interacts with the cytoplasmic domains of αIIb or β3 integrins, and Src kinase, and is involved in β3 integrin-mediated signal transduction.

BACKGROUND OF THE INVENTION

Integrins are a family of αβ heterodimers that mediate adhesion of cells to extracellular matrix proteins and to other cells (Clark et al., Science 268: 233–239, 1995). Integrins also participate in signal transduction, as evidenced by either an alteration in adhesive affinity of cell surface integrins in response to cellular activation (termed inside-out signal transduction) or by affecting intracellular signaling pathways following integrin-mediated adhesion (termed outside-in signal transduction). Many biological responses are dependent at least to some extent upon integrin-mediated adhesion and cell migration, including embryonic development, hemostasis, clot retraction, mitosis, angiogenesis, cell migration, inflammation, immune response, leukocyte homing and activation, phagocytosis, bone resorption, tumor growth and metastasis, atherosclerosis, restenosis, wound healing, viral infectivity, amyloid toxicity, programmed cell death and the response of cells to mechanical stress.

The integrin family consists of 15 related known α subunits (α1, α2, α3, α4, α5, α6, α7, α8, α9, αE, αV, αIIb, αL, αM, and αX) and 8 related known β subunits (β1, β2, β3, β4, β5, β6, β7, and β8). (Luscinskas et al., FASEB J. 8:929–938, 1994.) Integrin α and β subunits are known to exist in a variety of pairings. Integrin ligand specificity is determined by the specific pairing of the α and β subunits, although some redundancy exists as several of the integrins are known to bind the same ligand. Most integrins containing the β1, β2, β3, β5, β6, and β7 subunits have been found to transduce signals (reviewed by Hynes, Cell 69:11–25, 1992). Integrins are involved in both "inside-out" and "outside-in" signaling events.

Various pathologies associated with integrin-related defects are known. For example, inherited deficiencies of GP IIb–IIIa (also termed αIIbβ3) content or function have been described (termed Glanzmann's thrombasthenia) and are characterized by platelets that do not bind adhesive proteins and therefore fail to aggregate, resulting in a life-long bleeding diathesis. Inhibitors of the binding of fibrinogen and von Willebrand factor to GP IIb–IIIa have been described and have been found to block platelet aggregation in vitro and to inhibit clinical thrombosis in vivo (The EPIC Investigators, New England Journal of Med. 330:956–961, 1994; J. E. Tcheng et al., Circulation 91:2151–2157, 1995). Also, leukocyte adhesion deficiency (LAD) results from the absence of a β2 subunit, and is characterized by leukocytes which fail to bind β2 integrin ligands, resulting in individuals that are susceptible to infections.

The most studied platelet integrin αIIbβ3 (GPIIbIIIa) plays a critical role in homeostasis (platelet aggregation) and also in thrombosis. The αVβ3 plays a critical role in melanoma metastasis and angiogenesis, which is essential for cancer cell growth. The adhesion capacity of αIIbβ3 is known to be stimulated by various agonists such as thrombin, collagen, and ADP. This is termed inside-out signaling. There is accumulating evidence suggesting that integrins, in various cells and tissues including platelets, are also capable of mediating signals from the exterior to the cell interior, and that these signals can trigger cellular processes such as stimulating protein tyrosine phosphorylation, activating Na+/H+ antiporter, assembly of cytoskeletal structures and regulating gene expression that is involved in cell migration and proliferation. However, the mechanisms by which these signals are transmitted remain elusive. It has been hypothesized that the cytoplasmic tails of αIIbβ3 and other integrins may play important roles in adhesion by modulating the ligand-binding function of the extracellular domains through responses to intracellular signals generated by agonists stimulation (inside-out), and by mediating signals triggered by integrin receptor occupancy to intracellular molecules that may play a pivotal role in cellular physiological and pathological functions (outside-in).

A. Inside-Out Signaling

Inside-out signal transduction has been observed for β1, β2, and β3 integrins. (R. O. Hynes, Cell 69:11–25, 1992; D. R. Phillips, et al. Cell 65:359–362, 1991, S. S. Smyth et al., Blood 81:2827–2843, 1993; M. H. Ginsberg, et al. Thromb. Haemostasis 70:87–93, 1993; R. L. Juliano and S Haskill, J. Cell Biol. 120:577–585, 1993; E. Rouslahti, J. Clin. Invest. 87:1–5, 1991; Weber et al., J. Cell Biol. 134:1063–1073, 1996.)

Perhaps the most widely studied integrin that is involved in inside-out signaling is GP IIb–IIa, the receptor for four adhesive proteins, fibrinogen, von Willebrand factor, vitronectin and fibronectin that bind to stimulated platelets (D. R. Phillips, et al., Blood 71:831–43, 1988). The binding of adhesive proteins to GP IIb–IIIa is required for platelet aggregation and normal hemostasis and is also responsible for occlusive thrombosis in high shear arteries.

GP IIb–IIIa is known to be involved in inside-out signal transduction because GP IIb–IIIa on the surface of unstimulated platelets is capable of recognizing only immobilized fibrinogen. In response to platelet stimulation by agents such as thrombin, collagen and ADP, GP IIb–IIIa becomes a receptor for the four adhesive proteins identified in the previous paragraph, and the binding of fibrinogen and von Willebrand factor causes platelets to aggregate. A monoclonal antibody has been described which detects the activated, receptor competent state of GP IIb–IIIa, suggesting that the conformation of the receptor competent form of GP IIb–IIIa differs from that of GP IIb–IIIa which does not bind soluble fibrinogen or von Willebrand factor (S. J. Shattil, el al., J. Chem. Biol. 260:11107–11114, 1985). It has been postulated that inside-out GP IIb–IIIa signal transduction is dependent on cellular proteins that act to repress or stimulate GP IIb–IIIa activation (M. H. Ginsberg, et al., Curr. Opin. Cell Biol. 4:766–771, 1992).

β2 integrins on leukocytes also respond to inside-out signal transduction which accounts, for example, for the increased binding activity of LFA-1 ($\alpha L\beta_2$) on stimulated lymphocytes and the increased binding activity of MAC-1 ($\alpha m\beta_2$) on stimulated neutrophils (reviewed by T. Springer, Curr. Biol. 4:506–517, 1994).

B. Outside-In Signaling

Most integrins can be involved in outside-in signal transduction as evidenced by observations showing that binding of adhesive proteins or antibodies to integrins affects the activities of many cells, for example cellular differentiation, various markers of cell activation, gene expression, and cell proliferation (R. O. Hynes, Cell 69:11–25, 1992). The involvement of GP IIb–IIIa in outside-in signaling is apparent because the binding of unstimulated platelets to immobilized fibrinogen, a process mediated by GP IIb–IIIa, leads to platelet activation and platelet spreading (N. Kieffer and D. R. Phillips, *J. Cell Biol.* 113:451–461, 1991; Haimovich et al., *J. Biol. Chem.* 268:15868–15877, 1993).

Outside-in signaling through GP IIb–IIIa also occurs during platelet aggregation. Signaling occurs because fibrinogen or von Willebrand factor bound to the activated form of GP IIb–IIIa on the surface of stimulated platelets, coupled with the formation of platelet-platelet contacts, causes further platelet stimulation through GP IIb–IIIa signal transduction. In this manner, binding of adhesive proteins to GP IIb–IIIa can both initiate platelet stimulation or can augment stimulation induced by the other platelet agonists such as ADP, thrombin and collagen The binding of soluble fibrinogen to GP IIb–IIIa on unstimulated platelets can also be induced by selected GP IIb–IIIa antibodies such as LIBS6 (M-M. Huang et al., *J. Cell Biol.* 122:473–483, 1993): although platelets with fibrinogen bound in this manner are not believed to be stimulated, such platelets will aggregate if agitated and will become stimulated following aggregation through GP IIb–IIIa signal transduction.

Outside-in integrin signal transduction results in the activation of one or more cascades within cells. For GP IIb–IIIa, effects caused by integrin ligation include enhanced actin polymerization, increased $Na^+/H^+$ exchange, activation of phospholipases, increased phosphatidyl turnover, increased cytoplasmic $Ca^{++}$, and activation of kinases. Kinases known to be activated include PKC, myosin light chain kinase, src, syk and pp125FAK. Kinase substrates identified include pleckstrin, myosin light chain, src, syk, pp125FAK, and numerous proteins yet to be identified (reviewed in E. A. Clark and J. S. Brugge, *Sci.* 268:233–239, 1995). Many of these signaling events, including phosphorylations, also occur in response to ligation of other integrins (reviewed in R. O. Hynes, *Cell* 69:11–25, 1992). Although these other integrins have distinct sequences and distinct α-β parings that allow for ligand specificity, the highly conserved nature of the relatively small cytoplasmic domains, both between species and between subunits, predicts that related mechanisms will be responsible for the transduction mechanisms of many integrins.

C. Signal Transduction

The involvement of the cytoplasmic domain of GP IIb–IIIa in integrin signal transduction is inferred from mutagenesis experiments. Deletion of the cytoplasmic domain of GP IIb results in a constitutively active receptor that binds fibrinogen with an affinity equivalent to the wild-type complex, implying that the cytoplasmic tail of GP IIb has a regulatory role (T. E. O'Toole, et al., *Cell Regul.* 1:883–893, 1990). Point mutations, deletions and other truncations of GP IIb–IIIa affects the ligand binding activity of GP IIb–IIIa and its signaling response (P. E. Hughes, et al., *J. Biol. Chem.* 270:12411–12417, 1995; J. Ylanne, et al., *J. Biol. Chem.* 270:9550–9557, 1995).

Chimeric, transmembrane proteins containing the cytoplasmic domain of GP IIIa, but not of GP IIb, inhibit the function of GP IIb–IIa (Y. P. Chen et al., *J. Cell Biol.* 269:18307–18310, 1994), implying that free GP IIIa cytoplasmic domains bind proteins within cells which are necessary for normal GP IIb–IIIa function. Several proteins have been shown to bind either the transmembrane domains or the cytoplasmic domains of GP IIb or GP IIIa.

CD-9, a member of the tetraspanin family of proteins (F. Lanza, et al., *J. Biol. Chem.* 266:10638–10645, 1991), has been found to interact with GP IIb–IIIa on aggregated platelets. β3-endonexin, a protein identified through two hybrid screening using the cytoplasmic domain of GP IIIa as the "bait", has been found to interact directly and selectively with the cytoplasmic tail of GP IIIa (S. Shattil et al., *J. Cell. Biol.* 131:807–816, 1995). β3-endonexin shows decreased binding to the GP IIIa cytoplasmic domain containing the thrombasthenic S752-P mutation. It is not yet known whether either of these GP IIIa-binding proteins are involved in signal transduction.

Cytoplasmic proteins that bind to αVβ3 have also been described which may be interacting with the integrin at the GP IIIa cytoplasmic domain sequence. Bartfeld and coworkers (N. S. Bartfeld et al., *J. Chem. Biol.* 268:17270–17276, 1993) used immunoprecipitation from detergent lysates to show that a MW=190-kDa protein associates with the αV β3 integrin from PDGF-stimulated 3T3 cells. IRS-1 was found to bind to the αVβ3 integrin following insulin stimulation of Rat-1 cells stably transfected with DNA encoding the human insulin receptor (K. Vuori and E. Ruoslahti, *Sci.* 266:1576–1578, 1994). Kolanus et al. (*Cell* 86:233–242, 1996) recently identified Cytohesin-1. Cytohesin-1 specifically binds to the intracellular portion of the integrin β2 chain, and overexpression of cytohesin-1 induces β2 integrin-dependent binding of Jurkat cells to ICAM-1. A novel serine/threonine kinase, ILK-1, was found to associate with the β1 cytoplasmic domain (Hannigan et al., *Nature* 379:91–96, 1996). Overexpression of ILK-1 inhibits adhesion to the integrin ligands fibronectin, laminin, and vitronectin.

Integrin binding to adhesive proteins and integrin signal transduction have a wide variety of physiological roles, as identified above. Enhanced signaling through integrins allows for increased cell adhesion and activation of intracellular signaling molecules which causes enhanced cell mobility and growth, enhanced cell responsiveness, and modulations in morphological transformations. Although integrins responsible for cellular function have been described and signaling events are beginning to be elucidated, the mechanism by which integrins transduce signals remains to be determined.

To understand the molecular mechanisms of the inside-out and outside-in signaling roles mediated by the cytoplasmic tails of β3 integrin requires the identification of the intracellular molecules that interact with the intracellular tails of integrin. It has been reported that α-actinin binds to β1 tails in vitro (Otey et al. *J. Chem. Biol.* 268:21193–21197, 1993) but the functional relevance of these bindings is not clear. By using yeast two-hybrid, ILK-1 was identified as a β1interacting protein but ILK-1 does not bind to β3 (Hannigan et al., *Nature* 379:91–96 (1996). The present invention describes the molecular cloning of a novel human gene, Bap-1, encoding a protein, Bap-1, that associates with the integrin subunit αII and β3 cytoplasmic tails. Bap-1 was also found to associate with Src kinase. The molecular isolation of Bap-1 forms the basis for the development of therapeutic agents that modulate integrin-mediated signal transduction.

SUMMARY OF THE INVENTION

The present invention is based, in part, on the isolation and identification of a protein that binds to the cytoplasmic domain of the β3 subunit of integrins, hereinafter Bap-1 or the Bap-1 protein. Bap-1 was subsequently demonstrated to associate with the cytoplasmic domain of the αIIb subunit and Src kinase. Based on this observation, the present invention provides purified Bap-1 protein, useful in a variety of ways because of such associations.

The present invention further provides nucleic acid molecules that encode the Bap-1 protein. Such nucleic acid molecules can be in an isolated form, or can be operably linked to expression control elements or vector sequences.

The present invention further provides methods of identifying other members of the Bap-1 and/or Bap family of proteins. Specifically, the nucleic acid sequence of Bap-1 can be used as a probe, or to generate PCR primers, in methods to identify nucleic acid molecules that encode other members of the Bap-1 or Bap family of proteins.

The present invention further provides antibodies that bind to Bap-1. Such antibodies can be either polyclonal or monoclonal. Anti-Bap-1 antibodies can be used in a variety of diagnostic formats and for a variety of therapeutic methods.

The present invention further provides methods for reducing or blocking the association of an integrin with a cytoplasmic signaling partner. Specifically, the association of an integrin with a cytoplasmic signaling partner, such as Bap-1 or a Bap-1/signaling partner complex, e.g., Bap-1/Src kinase, can be blocked or reduced by contacting an integrin having a $\beta 3$ or $\alpha IIb$ subunit with an agent that blocks the binding of Bap-1 or the Bap-1/signaling partner complex to the integrin. The method can utilize an agent that binds to the cytoplasmic domain of the integrin or an agent that binds to Bap-1 or the Bap-1/signaling partner complex such as the Bap-1/Src complex.

Blocking integrin/Bap-1 associations can be used to modulate biological and pathological processes that require integrin mediated signals. Such methods and agents can be used to modulate cellular attachment or adhesion to a substrate or another cell, cellular migration, cellular proliferation and cellular differentiation. Pathological processes involving these actions include thrombosis, inflammation, tumor metastasis, wound healing and others noted above.

The present invention further provides methods for isolating integrin signaling partners that bind to Bap-1 or to a Bap-1/$\beta 3$ complex. Integrin signaling partners are isolated using the Bap-1 protein or the Bap-1/$\beta 3$ complex as a capture probe. Specifically, the Bap-1 protein, or a fragment thereof, or the Bap-1/$\beta 3$ complex, is mixed with an extract prepared from an integrin expressing cell under conditions that allow association of the Bap-1 protein, fragment, or complex with a signaling partner. Non-associated cellular constituents are removed from the mixture and the signaling partner is released from the capture probe. Alternatively, Bap-1 can be used as bait in the yeast two-hybrid system to screen an expression library and identify genes that encode proteins with the ability to bind to Bap-1 protein. Signaling partners isolated by these methods are useful in preparing antibodies and also serve as targets for drug development.

The present invention further provides methods to identify agents that can block or modulate the association of an integrin with Bap-1 or a signaling complex. Specifically, an agent can be tested for the ability to block, reduce or otherwise modulate the association of an integrin with Bap-1 or a signaling complex by incubating the Bap-1 protein, or a fragment thereof, with a $\beta 3$ integrin and a test agent and determining whether the test agent blocks or reduces the binding of the Bap-1 protein to the $\beta 3$ integrin. Agonists, antagonists and other modulators expressly are contemplated.

The biological and pathological processes that require Bap-1/integrin interaction can further be modulated using gene therapy methods. Additional genetic manipulation within an organism can be used to alter the expression of a Bap-1 gene or the production of a Bap-1 protein in an animal model. For example, a Bap-1-gene can be introduced into an individual deficient for Bap-1 to correct a genetic deficiency, peptide modulators of Bap-1 activity can be produced within a target cell using genetic transformation methods to introduce a modulator encoding nucleic acid molecules into a target cell, and Bap-1 can be inactivated in a non-human mammal to produce animal models of Bap-1 deficiency. The latter application, Bap-1-deficient animals, is particularly useful for identifying agents that modulate Bap-1 activity and other genes that encode proteins that interact with Bap-1. The use of nucleic acids for antisense and triple helix therapies and interventions are expressly contemplated.

The present invention further provides methods of reducing the severity of pathological processes that require integrin mediated signaling. Since association of Bap-1 or Bap-1 complex with a $\beta 3$ integrin is required for integrin-mediated signaling, agents that block integrin/Bap-1 association can be used in therapeutic methods.

BRIEF DESCRIPTION OF THE DRAWINGS

FIGS. 1A and 1B (SEQ ID NO: 1 and SEQ ID NO: 2) shows the nucleic acid sequence of human Bap-1 and the amino acid sequence of human Bap-1.

FIGS. 2A and 2B (SEQ ID NO: 3 and SEQ ID NO: 4) shows a partial nucleic acid of mouse Bap-1 and the amino acid sequence of mouse Bap-1.

DETAILED DESCRIPTION OF THE PREFERRED EMBODIMENT

I. General Description

The present invention is based in part on identifying a protein that binds to $\beta 3$ integrins and is involved in integrin-mediated signaling, hereinafter the Bap-1 protein. Bap-1 is also found to associate with the cytoplasmic tail of $\alpha IIb$ and Src kinase.

The Bap-1 protein can be used as an agent, or serve as a target for agents, that can be used to inhibit integrin mediated signaling, for example to inhibit biological processes requiring GP IIb–IIIa or $\alpha V\beta 3$ signal transduction.

The present invention is further based on the development of methods for isolating proteins that bind to Bap-1 or a Bap-1/$\beta 3$ or Bap-1/Src kinase complex. Probes based on the Bap-1 protein are used as capture probes to isolate Bap-1/integrin-associated signaling proteins. Dominant negative proteins, DNAs encoding these proteins, antibodies to these signaling proteins, peptide fragments of these proteins or mimics of these proteins may be introduced into cells to affect integrin function. Additionally, these proteins provide a novel target for screening of synthetic small molecules and combinatorial or naturally occurring compound libraries to discover novel therapeutics to regulate integrin function.

II. Specific Embodiments

A. Bap-1 Protein

The present invention provides isolated Bap-1 protein, as well as allelic variants of the Bap-1 protein, and conservative amino acid substitutions of the Bap-1 protein. As used herein, the Bap-1 protein (or Bap-1) refers to a protein that has the amino acid sequence of human Bap-1 depicted in FIG. 1B. The Bap-1 protein includes naturally occurring allelic variants of Bap-1, proteins that have a slightly different amino acid sequence than that specifically recited above. Allelic variants, though possessing a slightly different amino acid sequence than those recited above, will still have the requisite ability to associate with a β3 integrin as part of the relevant signaling cascade.

As used herein, the Bap-1 family of proteins refers to Bap-1 proteins that have isolated from organisms in addition to humans. One such member of the Bap-1 family of proteins is the mouse Bap-1 protein whose partial amino acid and nucleotide sequence is depicted in FIG. 2B. The methods used to identify and isolate other members of the Bap-1 family of proteins are described below and in Example 10.

As used herein, the Bap family of proteins refers to proteins that bind to β3 integrins, are structurally related to Bap-1, containing significant sequence homology to Bap-1. Members of the Bap family of proteins are involved in integrin-mediated signaling. For convenience, the Bap-1 protein, members of the Bap-1 family of proteins, and members of the Bap family of proteins are hereinafter referred to as the Bap proteins of the present invention.

The Bap proteins of the present invention are preferably in isolated form. As used herein, a protein is said to be isolated when physical, mechanical or chemical methods are employed to remove the Bap protein from cellular constituents that are normally associated with the Bap protein. A skilled artisan can readily employ standard purification methods to obtain an isolated Bap protein.

The Bap proteins of the present invention further include conservative variants of the Bap proteins herein described. As used herein, a conservative variant refers to alterations in the amino acid sequence that do not adversely affect the ability of the Bap protein to bind to a β3 integrin and mediate signaling. A substitution, insertion or deletion is said to adversely affect the Bap protein when the altered sequence prevents the Bap protein from associating with a β3 integrin. For example, the overall charge, structure or hydrophobic/hydrophilic properties of Bap can be altered without adversely affecting activity of Bap. Accordingly, the amino acid sequence of Bap can be altered, for example to render the peptide more hydrophobic or hydrophilic, without adversely affecting the ability of the peptide to become associated with β3 protegrin.

Ordinarily, the allelic variants, the conservative substitution variants, the members of the Bap family of proteins and especially the members of the Bap-1 family of proteins, will have an amino acid sequence having at least 75% amino acid sequence identity with the human or mouse Bap-1 sequence, more preferably at least 80%, even more preferably at least 90%, and most preferably at least 95%. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

Thus, the Bap proteins of the present invention include molecules having the amino acid sequences disclosed in FIG. 1B; fragments thereof having a consecutive sequence of at least about 3, 5, 10 or 15 amino acid residues of the Bap-1 protein; amino acid sequence variants of such sequence wherein an amino acid residue has been inserted N- or C-terminal to, or within, the disclosed Bap-1 sequence; amino acid sequence variants of the disclosed Bap-1 sequence, or their fragments as defined above, that have been substituted by another residue. Contemplated variants further include those containing predetermined mutations by, e.g., homologous recombination, site-directed or PCR mutagenesis, and the corresponding Bap proteins of other animal species, including but not limited to rabbit, rat, murine, porcine, bovine, ovine, equine and non-human primate species, and the alleles or other naturally occurring variants of the Bap family of proteins; and derivatives wherein the Bap protein has been covalently modified by substitution, chemical, enzymatic, or other appropriate means with a moiety other than a naturally occurring amino acid (for example a detectable moiety such as an enzyme or radioisotope).

As described below, members of the Bap family of proteins can be used: 1) to identify and isolate other integrin signaling partners that bind Bap-1 or a Bap-1/β3 complex, 2) in methods to identify agents that block the association of an integrin with Bap-1 or a Bap-1/signaling complex, 3) as a target to assay for integrin mediated signaling, and 4) as a therapeutic agent to block the association of an integrin with Bap-1 or a Bap-1/signaling complex.

B. Bap-1 Encoding Nucleic Acid Molecules

The present invention further provides nucleic acid molecules that encode Bap-1, and the related Bap proteins herein described, preferably in isolated form. As used herein, "nucleic acid" is defined as RNA or DNA that encodes a peptide as defined above, or is complementary to nucleic acid sequence encoding such peptides, or hybridizes to such nucleic acid and remains stably bound to it under appropriate stringency conditions, or encodes a polypeptide sharing at least 75% sequence identity, preferably at least 80%, and more preferably at least 85%, with the peptide sequences. Specifically contemplated are genomic DNA, cDNA, mRNA and antisense molecules, as well as nucleic acids based on alternative backbone or including alternative bases whether derived from natural sources or synthesized. Such hybridizing or complementary nucleic acid, however, is defined further as being novel and unobvious over any prior art nucleic acid including that which encodes, hybridizes under appropriate stringency conditions, or is complementary to nucleic acid encoding a Bap protein according to the present invention.

"Stringent conditions" are those that (1) employ low ionic strength and high temperature for washing, for example, 0.015M NaCl, 0.0015 M sodium titrate, 0.1% SDS at 50° C., or (2) employ during hybridization a denaturing agent such as formamide, for example, 50% (vol/vol) formamide with 0.1% bovine serum albumin, 0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS. A skilled artisan can readily determine and vary the stringency conditions appropriately to obtain a clear and detectable hybridization signal.

As used herein, a nucleic acid molecule is said to be "isolated" when the nucleic acid molecule is substantially separated from contaminant nucleic acid encoding other polypeptides from the source of nucleic acid.

The present invention further provides fragments of the Bap encoding nucleic acid molecule. As used herein, a fragment of a Bap encoding nucleic acid molecule refers to a small portion of the entire protein encoding sequence. The size of the fragment will be determined by the intended use. For example, if the fragment is chosen so as to encode an active portion of the Bap protein, the fragment will need to be large enough to encode the functional region(s) of the Bap protein. If the fragment is to be used as a nucleic acid probe or PCR primer, then the fragment length is chosen so as to obtain a relatively small number of false positives during probing/priming. If the fragment is chosen so as to bind the β3 integrin, the length will be chosen so as to contain the β3 contact site on the Bap protein.

Fragments of the Bap encoding nucleic acid molecules of the present invention (i.e., synthetic oligonucleotides) that are used as probes or specific primers for the polymerase chain reaction (PCR), or to synthesize gene sequences encoding Bap-1 proteins can easily be synthesized by chemical techniques, for example, the phosphotriester method of Matteucci, et al., (*J. Am. Chem. Soc.* 103:3185–3191, 1981) or using automated synthesis methods. In addition, larger DNA segments can readily be prepared by well known methods, such as synthesis of a group of oligonucleotides that define various modular segments of the Bap gene, followed by ligation of oligonucleotides to build the complete modified Bap gene.

The Bap encoding nucleic acid molecules of the present invention may further be modified so as to contain a detectable label for diagnostic and probe purposes. A variety of such labels are known in the art and can readily be employed with the Bap encoding molecules herein described. Suitable labels include, but are not limited to, biotin, radiolabeled nucleotides and the like. A skilled artisan can employ any of the art known labels to obtain a labeled Bap encoding nucleic acid molecule.

Modifications to the primary structure itself by deletion, addition, or alteration of the amino acids incorporated into the protein sequence during translation can be made without destroying the activity of the protein. Such substitutions or other alterations result in proteins having an amino acid sequence encoded by DNA falling within the contemplated scope of the present invention.

C. Isolation of Other Bap Encoding Nucleic Acid Molecules

As described above, the identification of the human and mouse Bap-1 encoding nucleic acid molecules allows a skilled artisan to isolate nucleic acid molecules that encode other members of the Bap-1 family of proteins in addition to the human and mouse sequence herein described. Further, the presently disclosed nucleic acid molecules allow a skilled artisan to isolate nucleic acid molecules that encode other members of the Bap family of proteins in addition to Bap-1.

Essentially, a skilled artisan can readily use the amino acid sequence of Bap-1 to generate antibody probes to screen expression libraries prepared from cells involved in integrin signaling. Typically, polyclonal antiserum from mammals such as rabbits immunized with the purified Bap-1 protein (as described below) or monoclonal antibodies can be used to probe a mammalian cDNA or genomic expression library, such as lambda gt11 library, to obtain the appropriate coding sequence for Bap-1, or other members of the Bap family of proteins. The cloned cDNA sequence can be expressed as a fuision protein, expressed directly using its own control sequences, or expressed by constructions using control sequences appropriate to the particular host used for expression of the enzyme. FIG. 1 identifies important antigenic and/or putative operative domains found in the Bap-1 protein sequence. Such regions are preferred sources of antigenic portions of the Bap-1 protein for the production of probe, diagnostic, and therapeutic antibodies.

Alternatively, a portion of the Bap-1 encoding sequence herein described can be synthesized and used as a probe to retrieve DNA encoding Bap-1 families of proteins from any mammalian organisms that possess integrin-mediated signaling pathways. Oligomers containing approximately 18–20 nucleotides (encoding about a 6–7 amino acid stretch) are prepared and used to screen genoric DNA or cDNA libraries to obtain hybridization under stringent conditions or conditions of sufficient stringency to eliminate an undue level of false positives.

Additionally, pairs of oligonucleotide primers can be prepared for use in a polymerase chain reaction (PCR) to selectively clone a Bap-encoding nucleic acid molecule. A PCR denature/anneal/extend cycle for using such PCR primers is well known in the art and can readily be adapted for use in isolating other Bap encoding nucleic acid molecules. FIG. 1A identifies regions of the human Bap-1 gene that are particularly well suited for use as a probe or as primers.

D. rDNA molecules Containing a Bap Encoding Nucleic Acid Molecule

The present invention further provides recombinant DNA molecules (rDNAs) that contain a Bap encoding sequence. As used herein, a rDNA molecule is a DNA molecule that has been subjected to molecular manipulation in situ. Methods for generating rDNA molecules are well known in the art, for example, see Sambrook et al., *Molecular Cloning* (1989). In the preferred rDNA molecules, a Bap encoding DNA sequence is operably linked to expression control sequences and/or vector sequences.

The choice of vector and/or expression control sequences to which one of the Bap encoding sequences of the present invention is operably linked depends directly, as is well known in the art, on the functional properties desired, e.g., protein expression, and the host cell to be transfonned. A vector contemplated by the present invention is at least capable of directing the replication or insertion into the host chromosome, and preferably also expression, of the Bap structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a Bap encoding nucleic acid molecule will include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Vectors that include a prokaryotic replicon can further include a prokaryotic or viral promoter capable of directing the expression (transcription and translation) of the Bap encoding gene sequences in a bacterial host cell, such as *E. coli*. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.), pPL and pKK223 available from Pharmacia, Piscataway, N.J.

Expression vectors compatible with eukaryotic cells, preferably those compatible with vertebrate cells, can also be used to form a rDNA molecules the contains a Bap encoding sequence. Eukaryotic cell expression vectors are well known in the art and are available from several commercial sources. Typically, such vectors are provided containing convenient restriction sites for insertion of the desired DNA segment. Typical of such vectors are PSVL and pKSV-10 (Pharmacia), pBPV-1/pML2d (International Biotechnologies, Inc.), pTDT1 (ATCC, #31255), the vector pCDM8 described herein, and the like eukaryotic expression vectors.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene. (Southern et al., *J. Mol. Anal. Genet.* 1:327–341, 1982.) Alternatively, the selectable marker can be present on a separate plasmid, and the two vectors are introduced by co-transfection of the host cell, and selected by culturing in the appropriate drug for the selectable marker.

E. Host Cells Containing an Exogenously Supplied Bap Encoding Nucleic Acid Molecule The present invention further provides host cells transformed with a nucleic acid molecule that encodes a Bap protein of the present invention. The host cell can be either prokaryotic or eukaryotic. Eukaryotic cells usefuil for expression of a Bap-1 protein are not limited, so long as the cell line is compatible with cell culture methods and compatible with the propagation of the expression vector and expression of the Bap-1 gene product. Preferred eukaryotic host cells include, but are not limited to, yeast, insect and mammalian cells, preferably vertebrate cells such as those from a mouse, rat, monkey or human fibroblastic cell line. Preferred eukaryotic host cells include Chinese hamster ovary (CHO) cells available from the ATCC as CCL61, NIH Swiss mouse embryo cells NIH/3T3 available from the ATCC as CRL 1658, baby hamster kidney cells (BHK), and the like eukaryotic tissue culture cell lines.

Any prokaryotic host can be used to express a Bap-encoding rDNA molecule. The preferred prokaryotic host is *E. coli*.

Transformation of appropriate cell hosts with a rDNA molecule of the present invention is accomplished by well known methods that typically depend on the type of vector used and host system employed. With regard to transformation of prokaryotic host cells, electroporation and salt treatment methods are typically employed, see, for example, Cohen et al., *Proc. Natl. Acad. Sci. USA* 69:2110, 1972; and Maniatis et al., *Molecular Cloning, A Laboratory Mammal*, Cold Spring Harbor Laboratory, Cold Spring Harbor, N.Y. (1982). With regard to transformation of vertebrate cells with vectors containing rDNAs, electroporation, cationic lipid or salt treatment methods are typically employed, see, for example, Graham et al., *Virol.* 52:456, 1973; Wigler et al., *Proc. Natl. Acad. Sci. USA* 76:1373–76, 1979.

Successfully transformed cells, i.e., cells that contain a rDNA molecule of the present invention, can be identified by well known techniques. For example, cells resulting from the introduction of an rDNA of the present invention can be cloned to produce single colonies. Cells from those colonies can be harvested, lysed and their DNA content examined for the presence of the rDNA using a method such as that described by Southern, *J. Mol. Biol.* 98:503, 1975, or Berent et al., *Biotech.* 3:208, 1985 or the proteins produced from the cell assayed via an immunological method.

F. Production of Bap using a rDNA molecule encoding a Bap Protein

The present invention further provides methods for producing a Bap protein that uses one of the Bap encoding nucleic acid molecules herein described. In general terms, the production of a recombinant form of a Bap protein typically involves the following steps:

First, a nucleic acid molecule is obtained that encodes a Bap protein, such as the nucleic acid molecule depicted in FIG. 1. If the Bap encoding sequence is uninterrupted by introns, it is directly suitable for expression in any host.

The Bap encoding nucleic acid molecule is then preferably placed in operable linkage with suitable control sequences, as described above, to form an expression unit containing the Bap encoding sequences. The expression unit is used to transform a suitable host and the transformed host is cultured under conditions that allow the production of the Bap protein. Optionally the Bap-1 protein is isolated from the medium or from the cells; recovery and purification of the protein may not be necessary in some instances where some impurities may be tolerated.

Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with Bap encoding sequences to produce Bap protein.

G. Methods to Identify Other Integrin Signaling Partners

Another embodiment of the present invention provides methods for use in isolating and identifying cytoplasmic signaling partners of integrins. Specifically, the Bap protein alone, or in combination with an integrin containing a β3 subunit (hereinafter a Bap/β3 complex), can be used to identify signaling partners that bind Bap or Bap/β3 complex from cells that express integrins.

In detail, a Bap protein alone, or in combination with an integrin containing a β3 subunit or Bap/β3 complex, is mixed with an extract or fraction of a cell that expresses an integrin under conditions that allow the association of a signaling partner with the Bap or Bap/β3 complex. After mixing, peptides that have become associated with Bap-1 or the Bap-1/β3 complex are separated from the mixture. The signaling partner that bound Bap-1 or the Bap-1/β3 complex can then be removed and further analyzed.

To identify and isolate a signaling partner, the entire Bap protein can be used. Alternatively, a fragment of a Bap protein can be used.

As used herein, a cellular extract refers to a preparation or fraction which is made from a lysed or disrupted cell. The preferred source of cellular extracts will be cells which naturally express β3 integrins. Examples of such cells include, but are not limited to platelets and leukocytes.

A variety of methods can be used to obtain an extract of a cell. Cells can be disrupted using either physical or chemical disruption methods. Examples of physical disruption methods include, but are not limited to, sonication and mechanical shearing. Examples of chemical lysis methods include, but are not limited to, detergent lysis and the enzyme lysis. A skilled artisan can readily adapt methods for preparing cellular extracts in order to obtain extracts for use in the present methods.

The cellular extract can be prepared from cells that have been freshly isolated from a subject or from cells or cell lines which have been cultured. In addition, the extract can be prepared from cells that are either in a resting state or from cells that have been activated. A variety of agents can be used to activate a cell. The selection of an activating agent will be based on the cell type used. For example, thrombin, collagen or ADP can be used to activate platelets while PMA can be used to activate leukocytes.

Once an extract of a cell is prepared, the extract is mixed with the Bap protein, or a Bap/β3 complex, under conditions in which association of the Bap or Bap/β3 complex with the signaling partner can occur. A variety of conditions can be used, the most preferred being conditions that closely resemble conditions found in the cytoplasm of an integrin-expressing cell. Features such as osmolarity, pH, temperature, and the concentration of cellular extract used, can be varied to optimize the association of the integrin with the signaling partner.

After mixing under appropriate conditions, Bap or the Bap/β3 complex is separated from the mixture. A variety of techniques can be utilized to separate the mixture. For example, antibodies specific to Bap or the Bap/β3 complex can be used to immunoprecipitate the Bap or Bap/β3 complex and associated signaling partner. Alternatively, standard chemical separation techniques such as chromatography and density/sediment centrifugation can be used.

After removal of nonassociated cellular constituents found in the extract, the signaling partner can be dissociated from the Bap or Bap/β3 complex using conventional methods. For example, dissociation can be accomplished by altering the salt concentration or pH of the mixture.

To aid in separating associated integrin/signaling partner pairs from the mixed extract, the Bap or Bap/β3 complex can be immobilized on a solid support. For example, Bap can be attached to a nitrocellulose matrix or acrylic beads. Attachment of Bap to a solid support aids in separating peptide/signaling partner pair from other constituents found in the extract.

The identified signaling partners can be either a single protein or a complex made up of two or more proteins.

Alternatively, the Bap-encoding nucleic acid molecule can be used in a yeast two-hybrid system. The yeast two-hybrid system has been used to identify other protein partner pairs and can readily be adapted to employ the Bap encoding molecules herein described. (See Example 2.)

H. Use of Bap and Other Isolated Signaling Partners

Once isolated, the integrin signaling partners obtained using the above described method, as well as the Bap proteins herein described, especially Bap-1, can be used for a variety of purposes. These proteins can be used to generate antibodies that bind to the Bap protein, or the signaling partner, using techniques known in the art. Antibodies that bind Bap or another integrin signaling partner can be used to assay integrin signaling, as a therapeutic agent to modulate a biological or pathological process mediated by integrin signaling, or to purify the signaling partner. These uses are described in detail below.

I. Methods to Identify Agents that Block Integrin Cytoplasmic Signaling Partner Interactions Another embodiment of the present invention provides methods for identifying agents that reduce or block the association of an integrin with a cytoplasmic signaling complex, such as a Bap protein or a Bap/signaling partner complex, hereinafter collectively referred to as Bap signaling complex. Specifically, a β3 integrin is mixed with a Bap protein, a cellular extract containing Bap, or a complex of Bap and the signaling partner described above, in the presence and absence of an agent to be tested. After mixing under conditions that allow association of the integrin or peptide with the Bap signaling complex, the two mixtures are analyzed and compared to determine if the agent reduced or blocked the association of the integrin with the Bap signaling complex. Agents that block or reduce the association of an integrin with the Bap signaling complex will be identified as decreasing the amount of association present in the sample containing the tested agent.

As used herein, an agent is said to reduce or block integrin/Bap signaling complex association when the presence of the agent decreases the extent to which or prevents the Bap signaling complex from becoming associated with the β3 integrin. One class of agents will reduce or block the association by binding to the Bap signaling complex while another class of agents will reduce or block the association by binding to the β3 integrin.

The Bap signaling complex used in the above assay can either be an isolated and fully characterized protein, such as Bap-1, or can be a partially characterized protein that binds to Bap-1 or a Bap-1/signaling partner complex that has been identified as being present in a cellular extract. It will be apparent to one of ordinary skill in the art that so long as the Bap signaling complex has been characterized by an identifiable property, e.g., molecular weight, the present assay can be used.

Agents that are assayed in the above method can be randomly selected or rationally selected or designed. As used herein, an agent is said to be randomly selected when the agent is chosen randomly without considering the specific sequences involved in the association of the integrin with the Bap signaling complex. An example of randomly selected agents is the use a chemical library or a peptide combinatorial library, or a growth broth of an organism.

As used herein, an agent is said to be rationally selected or designed when the agent is chosen on a nonrandom basis which takes into account the sequence of the target site and/or its conformation in connection with the agent's action. As described above, there are two sites of action for agents that block integrin/Bap signaling complex interaction: the cytoplasmic domain of the β3 subunit or the Bap signaling complex. Agents can be rationally selected or rationally designed by utilizing the peptide sequences that make up the contact sites of the integrin/Bap signaling complex pair. For example, a rationally selected peptide agent can be a peptide whose amino acid sequence is identical to the Bap-1 contact site on the cytoplasmic domain of the integrin or the β33 contact site on Bap-1. Such an agent will reduce or block the association of the integrin with the signaling partner by binding to Bap-1 or the β3 integrin respectively.

The agents of the present invention can be, as examples, peptides, small molecules, vitamin derivatives, as well as carbohydrates. A skilled artisan can readily recognize that there is no limit as to the structural nature of the agents of the present invention.

One class of agents of the present invention are peptide agents whose amino acid sequences are chosen based on the amino acid sequence of the cytoplasmic domain of the β3 subunit or the amino acid sequence of the Bap protein, such as the human Bap-1 sequence depicted in FIG. 1B.

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies immunoreactive with critical positions of the cytoplasmic domain of an integrin or with a Bap signaling complex such as Bap-1. Antibody agents are obtained by immunization of suitable mammalian subjects with peptides, containing as antigenic regions, those portions of the β3 cytoplasmic domain or Bap signaling complex, intended to be targeted by the antibodies. Critical regions include the contact sites involved in the association of the integrin with the Bap signaling complex.

Antibody agents are prepared by immunizing suitable mammalian hosts in appropriate immunization protocols using the peptide haptens alone, if they are of sufficient length, or, if desired, or if required to enhance immunogenicity, conjugated to suitable carriers. Methods for preparing immunogenic conjugates with carriers such as BSA, KLH, or other carrier proteins are well known in the art. In some circumstances, direct conjugation using, for example, carboduimide reagents may be effective; in other instances linking reagents such as those supplied by Pierce Chemical Co., Rockford, Ill., may be desirable to provide accessibility to the hapten. The hapten peptides can be extended at either the amino or carboxy terminus with a Cys residue or interspersed with cysteine residues, for example, to facilitate linking to a carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler and Milstein or modifications which effect immortalization of lymphocytes or spleen cells, as is generally known. The immortalized cell lines secreting the desired antibodies are screened by immunoassay in which the antigen is the peptide hapten or is the integrin or signaling complex itself When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of F(ab')$_2$ fragments is often preferable, especially in a therapeutic context, as these fragments are generally less immunogenic than the whole immunoglobulin.

The antibodies or fragments may also be produced, using current technology, by recombinant means. Regions that bind specifically to the desired regions of receptor can also be produced in the context of chimeras with multiple species origin.

The antibodies thus produced are useful not only as modulators of the association of an integrin with a Bap signaling complex, but are also useful in immunoassays for detecting integrin mediated signaling and for the purification of integrin-associated signaling proteins.

J. Uses for Agents that Block the Association of an Integrin with a Bap Signaling Complex As provided in the Background section, integrins play important roles in intracellular signaling, cellular attachment, cellular aggregation and cellular migration. Agents that reduce or block the interactions of an integrin with a Bap signaling complex can be used to modulate biological and pathologic processes associated with integrin function and activity.

In detail, a biological or pathological process mediated by an integrin can be modulated by administering to a subject an agent that blocks the interaction of an integrin with a Bap signaling complex.

As used herein, a subject can be any mammal, so long as the mammal is in need of modulation of a pathological or biological process mediated by an integrin. The term "mammal" is meant an individual belonging to the class Mammalia. The invention is particularly useful in the treatment of human subjects.

As used herein, a biological or pathological process mediated by an integrin or integrin signaling refers to the wide variety of cellular events in which an integrin binds a substrate producing an intracellular signal that involves the Bap protein or a Bap signaling complex. Examples of biological processes include, but are not limited to, cellular attachment or adhesion to substrates and other cells, cellular aggregation, cellular migration, cell proliferation, and cell differentiation.

Pathological processes refer to a category of biological processes which produce a deleterious effect. For example, thrombosis is the deleterious attachment and aggregation of platelets while metastasis is the deleterious migration and proliferation of tumor cells. These pathological processes can be modulated using agents which reduce or block integrin/Bap signaling complex association.

As used herein, an agent is said to modulate a pathological process when the agent reduces the degree or severity of the process. For example, an agent is said to modulate thrombosis when the agent reduces the attachment or aggregation of platelets.

Two known parings of the β3 subunit have been observed: with αV to make αVβ3, the Vitronectin Receptor; and with GP IIb to make GP IIb–IIIa, the Fibrinogen Receptor. αVβ3 is widely distributed, is the most promiscuous member of the integrin family and mediates cellular attachment to a wide spectrum of adhesive proteins, mostly at the R-G-D sequence on the adhesive protein. The biological processes mediated by αVβ3 are diverse and include bone resorption, angiogenesis, tumor metastasis and restenosis. αVβ3 is known to signal upon adhesive protein ligation (P. I. Leavesley, et al., *J. Cell Biol.* 121: 163–170, 1993). As an example, endothelial cells undergo apoptosis when relieved of ligation (P. C. Brooks, *Cell* 79:1157–1164, 1994).

GP IIb–IIIa, by contrast, is restricted to platelets and cells of megakaryocyte lineage although a report has appeared indicating that GP IIb–IIIa is present in tumor cell lineages. As discussed in detail elsewhere in this application, the function of GP IIb–IIIa is primarily to bind adhesive proteins to mediate platelet aggregation. In this function, GP IIb–IIIa participates in both inside-out and outside-in signaling. Decreased receptor function of GP IIb–IIIa leads to bleeding; elevated receptor function of GP IIb–IIIa can lead to thrombus formation. Studies have appeared indicating that platelet aggregation through GP IIb–IIIa may also be involved in tumor metastasis.

K. Administration of Agents that Affect Integrin Signaling

The agents of the present invention can be provided alone, or in combination with another agents that modulate a particular pathological process. For example, an agent of the present invention that reduces thrombosis by blocking integrin mediated cellular signaling can be administered in combination with other anti-thrombotic agents. As used herein, two agents are said to be administered in combination when the two agents are administered simultaneously or are administered independently in a fashion such that the agents will act at the same time.

The agents of the present invention can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The present invention further provides compositions containing one or more agents which block integrin/signaling complex association. While individual needs vary, determination of optimal ranges of effective amounts of each component is within the skill of the art. Typical dosages comprise 0.1 to 100 $\mu$g/kg body wt. The preferred dosages comprise 0.1 to 10 $\mu$g/kg body wt. The most preferred dosages comprise 0.1 to 1 $\mu$g/kg body wt.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

In practicing the methods of this invention, the compounds of this invention may be used alone or in combination, or in combination with other therapeutic or diagnostic agents. In certain preferred embodiments, the compounds of this invention may be coadministered along with other compounds typically prescribed for these conditions according to generally accepted medical practice, such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of this invention can be utilized in vivo, ordinarily in mammals, such as humans, sheep, horses, cattle, pigs, dogs, cats, rats and mice, or in vitro.

L. Methods for Identifying Integrin-Mediated Signaling

The present invention further provides methods for identifying cells involved in integrin-mediated signaling as well as techniques that can be applied to diagnose biological and pathological processes associated with integrin-mediated signaling. Specifically, integrin-mediated signaling can be identified by determining whether the Bap protein, or Bap signaling complex, is expressed and/or is associated with a $\beta 3$ integrin. Cells expressing Bap or the Bap signaling complex, or in which Bap or the Bap signaling complex is associated with a $\beta 3$ integrin are considered to be involved in integrin-mediated signaling. Such methods are useful in identifying sites of inflammation, thrombosis, angiogenesis and tumor metastasis.

In one example, an extract of cells is prepared which contains the $\beta 3$ integrin. The extract is then assayed to determine whether the $\beta 3$ integrin is associated with Bap or a Bap signaling complex. The degree of association present provides a measurement of the degree of signaling the cell is participating in. An increase in the degree of signaling is a measurement of the level of integrin mediated activity.

For example, to determine whether a tumor has metastatic potential, an extract is made of the tumor cells and the $\beta 3$ integrins expressed by the tumor cells are isolated using known methods such as immunoprecipitation. The integrins are then analyzed, for example, by gel electrophoresis to determine whether a Bap protein is associated with the integrin. The presence and level of a Bap association correlates with the metastatic potential of the cancer.

Alternatively, the level of Bap protein or Bap gene expression can be used to directly correlate with the involvement of the cell in integrin-mediated signaling. A variety of immunological and nucleic acid techniques can be used to determine if the Bap protein, or a Bap encoding mRNA, is produced in a particular cell. The presence of increased levels of the Bap protein or the Bap encoding MRNA, correlates with the metastatic potential of the cancer.

M. Gene Therapy

The Bap gene and the Bap protein can also serve as a target for gene therapy in a variety of contexts. For example, in one application, Bap-deficient non-human animals can be generated using standard knock-out procedures to inactivate a Bap gene. In such a use, a non-human mammal, for example a mouse or a rat, is generated in which a member of the Bap family of genes is inactivated. This can be accomplished using a variety of art-known procedures such as targeted recombination. Once generated, the Bap-deficient animal can be used to 1) identify biological and pathological processes mediated by Bap, 2) identify proteins and other genes that interact with Bap, 3) identify agents that can be exogenously supplied to overcome Bap deficiency and 4) serve as an appropriate screen for identifying mutations within Bap that increase or decrease activity.

In addition to animal models, human Bap-deficiency can be corrected by supplying to a human, a genetic construct that encodes the Bap protein which is deficient in the subject. A variety of techniques are presently available, and others are being developed, for introducing a nucleic acid molecule into a human subject to correct a genetic deficiency. Such methods can be readily adapted to employ the Bap-encoding nucleic acid molecules of the present invention.

In another embodiment, genetic therapy can be used as a means for modulating a Bap-mediated biological or pathological processes. For example, during graft rejection, it may be desirable to introduce into the subject being treated a genetic expression unit that encodes a modulator of Bap-1/integrin mediated signaling, such as an antisense encoding nucleic acid molecule. Such a modulator can either be constitutively produced or inducible within a cell or specific target cell. This allows a continual or inducible supply of a therapeutic agent within the subject.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

Other generic configurations will be apparent to one skilled in the art.

EXAMPLES

Example 1

Cloning of Bap-1

A yeast two-hybrid system (Chien et al., *Proc. Natl. Acad. Sci. USA* 88:9578–9582, 1991) was used to identify proteins that interact specifically with the cytoplasmic tail of the β3 integrin subunit. The histidine selection system (Durfee et al., *Genes. Dev.* 7:555–569, 1993), which utilizes two distinct GAL4-dependent reporter genes, HIS3 and 1acZ was employed. The bait was the β3 cytoplasmic domain fused to the GAL4 DNA binding domain of vector pGBT9. The new construct was designated as pGBT9-IIIa. Approximately $5 \times 10^5$ primary transformants of mouse embryo cDNA library expressed as fusion products with the VP16 activation domain (Vojtek et al., *Cell.* 74:205–214, 1993) were screened. Several hundreds clones showed significant histidine prototrophy and of these 20 were strongly β-galactosidase positive. For two of these clones( 126-2 and 141-1) histidine prototrophy and β-galactosidase activity depended on the presence of both plasmids. As a fuirther control, segregants containing the cDNA library plasmids only were mated with cells expressing GAL4 DNA binding protein only (pGBT9) and several tester GAL4 DNA binding protein fusions including v-Raf and mutant v-Raf (Li et al., *EMBO* 14:685–696, 1995). Histidine prototrophy and β-galactosidase activity were recovered only in combination with original pGBT9-IIIa.

The cDNA library plasmid DNA of 126-2 and 141-1 were transformed into *E. coli* and subjected to DNA sequencing. The sequence data showed that the inserts of these two clones are from one single gene, and a search of the GenBank database revealed that this gene is not represented in the database. DNA sequencing showed that neither of the cDNA clones contain a complete protein coding region. To clone the full-length cDNA of the 126-2 human homologue, a human bone marrow 5'-stretch plus 1 gt11 cDNA library (Clontech, CAT HL5005b) were screened using a 400 bp NotI fragment isolated from clone 126-2 as probe. Approximately $5 \times 10^5$ clones were screened and two positive clones, gt5 and gt6, were identified. The two clones were amplified using standard techniques. DNA were prepared and the inserts were subcloned into pBSKSII, cut at the NotI site. The clone containing the NotI fragment from gt5 was designated pBSgt5, and the clone containing the NotI insert from phage gt6 was designated pBSgt6. Restriction mapping and preliminary sequencing indicated that pBSgt6 has an insert of 3.5 kbp, and pBSgt5 has an insert of 2.1 kbp, contained within pBSgt6. The cDNA insert of the pBSgt6 was subjected to sequencing analysis, and was shown to have a size of 3.5 kbp containing an open reading frame.

Example 2

Bap-1 Interacts with αIIb and v-Src Kinase in the Yeast Two-Hybrid System

A spectrum of proteins of the integrin family or mutants, and some potential signaling molecules, were tested for their ability to interact with Bap-1 in the yeast two-hybrid system. Bap-1 was demonstrated to interact with the cytoplasmic tail of αIIb and v-Src tyrosine kinase, but not with the cytoplasmic tail of β2, β3(S752P) serine to proline mutant, or a β3/β1 chimera. Further, Bap-1 was seen to interact with Bap-1 in the two-hybrid, suggesting that a functional homodimer may be formed within cells. The results indicate that Bap-1 might link integrin αIIbβ3 signal transduction by bridging other known signaling molecules such as pp60src kinase. Src kinase, a major platelet tyrosine kinase, is speculated to be involved in tyrosine-specific phosphorylation of cellular proteins during platelet activation by different agonists. Src kinase was shown to phosphorylate the β3 integrin in vitro (Law et al., *J. Chem. Biol.* 271:10811–10815, 1996). 40% of total platelet pp60src becomes associated with the cytoskeletal fraction upon platelet activation (Horvath et al., *EMBO J.* 11:855–861, 1992). Thrombin stimulation of platelets induces a transient increase in the specific activity of pp60c-src followed by a redistribution of pp60csrc to the triton X-100-insoluble, cytoskeleton-rich fraction (Clark et al., *Molec. Cell Biol.* 13:1863–1871, 1993). This association requires platelet aggregation and actin polymerization (Oda et al., *J. Biol. Chem.* 267:20075–20081, 1992). The present findings implicate Bap-1 as involved in both outside-in and inside-out signaling by bridging integrins with protein tyrosine kinases.

Example 3

Analysis of Mouse Bap-1

Bap-1 encodes a protein of 336 amino acids with a RING finger domain. Analysis of the protein sequence of the Bap-1 identifies an unusual amino-terminal RING finger motif that can be written as CX2CX11ECLHXFCX2CX11CX2 (SEQ ID NO: 5). The proteins that share a RING domain have been reported to be implicated during development, such as DG17 (Driscoll and Williams, *MCB* 7:4482–4489, 1987) and Posterior Sex Combs and Suppressor two of zeste (Brunk et al., *Nature* 353:351–353, 1991; Lohuizen et al., *Nature* 353:353–355, 1991), gene transcription such as RPT-1 (Patarca et al., *Proc. Natl. Acad. Sci.* 85:2733–2737, 1988), DNA repair such as RAD-18 (Jones et al., *Nucleic Acids Res.* 16: 7119–7131, 1988), oncogenic transformation such as BMI-1 (Haupt et al., *Cell* 65:753–763, 1991), tumor suppression such as BRCA-1 (Miki et al., *Science* 266: 66–71, 1994), and signal transduction such as CD40-binding protein (CD40-bp) (Hu et al., *J. Biol. Chem.* 269:30069–30072, 1994) and TRAF2 (Rothe et al., *Cell* 78:681–692, 1994; Hsu et al., *Cell* 84:299–308, 1996). The solution structure of the RING finger domain from the acute promyelocyte leukemia pro-oncoprotein PML suggested that the PML RING finger is involved in making protein-protein interactions (Borden et al., 1995. *EMBO J.* 14: 1532–1541), a molecular mechanism which is commonly used in signaling protein complexes.

Bap-1 has significant sequence similarity with the ring1 gene, i.e., it has 48% identity with RING1 gene at amino acid level, the function of which is not known. Interestingly, Bap-1 shares 17% identity with Drosophila gene Posterior Sex Combs (Psc) that is believed to be homologous to oncogene bmi-1, that was originally found to be involved in B- and T- cell lymphoma. Psc is a member of the Polycomb-group gene family, which is required to maintain the repression of homeotic genes that regulate the identities of Drosophila segments. bmi-1 appeared to play a similar role in vertebrates: bmi-1 knock-out mice shows posterior transformations of the axial skeleton (van der Lugt et al., Genes & Dev. 8: 757–769, 1994); and overexpression of bmi-1 in mice shows the opposite phenotype, a dose-dependent anterior transformation of vertebral identity (Aldema et al., Nature 374:724–727, 1995). Both the Psc and bmi-1 can repress activator function when transiently introduced into cells (Bunker and Kingston, Molec. Cell Biol. 14: 1721–1732, 1994). Furthermore mel-18, another Polycomb group-related mammalian gene which shares an amino acid sequence including RING-finger motif, can function as a transcriptional negative regulator with tumor suppressor activity.

All this suggests that the Bap-1 protein may play an important role in cell migration, cell proliferation, and development, for which the role of integrins is implicated. For example, the Bap-1 protein may function as a latent transcriptional regulator, either positive or negative, that is inactive when bound to the β3 cytoplasmic tail of integrins, but can be activated by outside-in or inside-out signaling and then dissociates from the tail and translocates into the nucleus.

Example 4

Tissue Distribution of Bap-1

The tissue distribution of Bap-1 expression was examined by Northern blot, and it was found that Bap-1 is expressed in most tissues, consistent with a suggestion that Bap-1 has an important role in cellular functions. In addition to the 3.6 kb mRNA, we detected a 2.4 kb size mRNA in most tissues, which might be a spliced form of Bap-1, or a Bap-related gene.

Clone 126-2, the partial cDNA of the mouse homologue of Bap-1, was located in the central part of the Bap-1, and is 98% identical with Bap-1. Again, the high degree of conservation suggest a fundamental role for Bap-1 in cellular regulation.

Interaction between Bap-1 and the cytoplasmic tail observed in the yeast two-hybrid is unlikely to be mediated by a yeast protein. This was further demonstrated by an in vitro binding assay using purified αIIbβ3 and purified Bap-1 protein. Specifically, Bap-1 was expressed as a GST-Bap-1 fusion protein in E. coli, and purified and immobilized on glutathione agarose beads. The immobilized GST-Bap-1 fusion was then incubated with purified αIIbβ3, and retention on the beads was analyzed by SDS-PAGE and Western Botting. The results showed that β3 protein binds specifically to GST-Bap-1, but not to GST controls. The ability to confirm the binding between Bap-1 and the β3 cytoplasmic tail in vitro is consistent with the robust interaction observed in the yeast two-hybrid system.

Example 5

Expression of Bap-1 in a Heterologous System

CHO cells expressing αIIbβ3, like in platelets, manifest highly regulated changes in the ligand binding affinity as measured by PAC-1 binding. The CHO cell heterologous system facilitated the analysis of recombinant gene functions in the role of regulating the αIIbβ3 affinity. An example of this type of analysis is that CHO cells expressing αIIbβ3 were shown to be activated by recombinant R-Ras. (Zhang et al., Cell 85:61–69, 1996) To look at the effects of Bap-1 on the regulation of αIIbβ3, αIIbβ3 is co-expressed with the Bap-1 proteins, and deletion variants of Bap-1, and the cellular phenotypes are examined accordingly.

Two different strategies can be used to reduce endogenous Bap-1 activity/production; namely using an antisense Bap-1 molecule or using an inhibitory mutant of Bap-1. The RING domain in the TRAF2 and PML proteins have been implicated as involving protein-protein interactions. In the case of TRAF2, the RING deletion mutant functions as a dominant-negative inhibitor of TNF-mediated NF-KB activation (Cell 84:299–308). Accordingly, RING deletion may block or activate Bap-1 depending on the nature of the molecules that associate with the Bap-1 RING domains. To this end, Bap-1 and variants thereof, have been flag-tagged and inserted into mammalian expression vectors. Stable cell lines that express the wild-type Bap-1, Bap-1 variants (such as the RING deletion mutant Bap-1), the Bap-1 anti-sense RNA, and the vector control can be generated using standard transformation methods. The expression of Bap-1 can be determined by anti-flag and anti-Bap-1 antibodies. The cell lines can then be examined for the effect on the activation of αIIbβ3 (PAC-1 binding), cell spreading, and attachment on fibrinogen. Over-expression of a signaling molecule such as Bap-1 can desensitize the regulatory pathway. Therefore, transient and/or conditional expression can also be exploited to characterize the functions of the Bap-1 gene.

Example 6

Effects of Bap-1 on the αVβ3 Functions on Melanoma

Since the expression of Bap-1 is not restricted to αIIbβ3 expressing cells such as platelets, Bap-1 is likely to be involved in the αVβ3 functions. To this end, Bap-1 and variants thereof can be transfected into an αVβ3 expressing cell line such as M21 melanoma. Again, the adhesive properties such as attachment and spreading on vitronectin can be examined. The expression of αVβ3 in M21 melanoma is essential for metastasis.

Example 7

The Cellular Localization of Bap-1

The cellular localization of Bap can be examined by in situ immunohistochemistry. Anti-Bap-1 monoclonal antibodies, particularly antibodies generated against 1) a GST-Bap-1 fusion protein expressed and purified in E. coli, 2) a 26mer N-terminal peptide corresponding to a unique region of Bap-1 protein, and/or 3) a 26mer peptide corresponding to the central part of the protein can be readily generated and used in the immunohistochemical examination of Bap-1 production/expression. The tissue distribution of Bap-1 can be examined using these Bap-1 antibodies.

Example 8

Bap-1/β3 Interaction In Vivo

To confirm the interaction observed in the yeast two-hybrid system described above and in vitro, anti-Bap-1 antibodies can be used to immunoprecipitate Bap-1 and SDS-PAGE can be used for further purification. Then the presence of β3 can be detected by Western blotting using anti-β3 antibodies. The reverse experiment can also be performed by immunoprecipitating β3 and blotting with anti-flag or anti-Bap-1 antibodies.

Example 9

Identification of the Domains and Amino Acids that are Critical for Protein-Protein Interaction The critical residues both in the β3 tail and in the Bap-1 protein can be further identified by deletion and mutagenesis analysis. In one application, these experiments are done in a heterologous cell using the yeast two-hybrid system described above.

Example 10

Cloning of Bap-1 Related Genes by PCR or Library Screening

A messenger RNA of 2.4 kb in size, in addition to the 3.5 kb Bap-1 mRNA, was observed in most tissues examined by Northern blot using the human Bap-1 cDNA or the mouse partial cDNA as probe. These results suggested that there are Bap-1 related genes or spliced forms expressed. The Bap-1 related genes can be readily isolated using Bap-1 cDNA as probe to screen cDNA libraries, genomic libraries, or can be used to design primers based on the Bap-1 DNA sequence. The isolated genes can then be examined for their functions in integrin signaling as detailed in the other examples listed in this application.

Genomic studies of Bap-1 gene: The human chromosomal Bap-1 gene can be isolated by conventional approaches, and its genomic structure and chromosome location can be determined. A genomic database can be searched to determine if its chromosome location corresponds to any disease locus.

Example 11

Oncogenic or Tumor Suppressor Activity of Bap-1

Oncogenic transformation is often accompanied by deregulation of integrin signaling, such as an increase or decrease of cell adhesion. It is interesting to note that Bap-1 has amino acid similarity to proto-oncogene Bmi-1 and tumor suppressor gene Mel-18. Accordingly, the oncogenic or tumor suppressor activity of Bap-1 can be tested. Briefly, Bap-1 and its variants are transfected into Rat-1 or NIH3T3 cells, and soft agar growth and focus formation are scored, both of which are indicative of oncogenic activity. To test tumor suppressor activity of Bap-1, Bap-1 and its variants are co-transfected with a series of known oncogenes into Rat-1 or NIH3T3 cells. and the effects of Bap-1 on the oncogenic transformation of known oncogenes are examined.

Tumor metastasis requires angiogenesis, and integrin αvβ3 is essential for angiogenesis. By blocking αVβ3 signaling such as by modulating Bap-1/β3 interaction, tumor metastasis can be inhibited.

Example 12

Generation of Bap-1 Homozygous Deficient Mice

Routine genetic procedures can be used to create genetic knock-out mutants of mice in which Bap-1 has been inactivated. The preferred method is to introduce, using targeted homologous recombination, a nucleic acid molecule that contains multiple stop codons in each reading frame. This serves to inactivate the Bap-1 locus. Such mice can be used to further study biochemical and physiological effects of Bap-1.

---

What is claimed:

1. An isolated nucleic acid molecule that encodes the amino acid sequence of SEQ ID NO:2.

2. The isolated nucleic acid molecule of claim 1, wherein said nucleic acid molecule is operably linked to one or more expression control elements.

3. The isolated nucleic acid molecule of claim 1, wherein said nucleic acid molecule is included in a vector.

4. A host transformed to contain the nucleic acid molecule of claim 1.

5. The host of claim 4, wherein said host is selected from the group consisting of prokaryotic hosts and eukaryotic hosts.

6. A method for producing a Bap-1 protein comprising the step of culturing a host transformed with the nucleic acid molecule of claim 2 under conditions in which the Bap-1 protein is expressed.

7. The method of claim 6, wherein said host is selected from the group consisting of prokaiyotic hosts and eukaryotic hosts.

8. An isolated nucleic acid molecule comprising a nucleotide sequence selected from the group consisting of SEQ ID NO:1 and a fragmnent of SEQ ID NO:1, wherein said fragment encodes SEQ ID NO:2.

9. A nucleic acid molecule consisting of the nucleotide sequence of SEQ ID NO:1 or a fragment of SEQ ID NO:1, wherein said fragment encodes SEQ ID NO:2.

10. A vector comprising the nucleic acid molecule of any of claims 8 or 9.

11. A host transformed to contain the vector of claim 10.

12. A host transformed to contain a nucleic acid molecule of any of claims 8 or 9.

13. A method for producing a Bap protein comprising the step of culturing a host of claim 11 under conditions in which the Bap protein is expressed.

14. A method for producing a Bap protein comprising the step of culturing a host of claim 12 under conditions in which the Bap protein is expressed.

15. The host of claim 11, wherein said host is selected from the group consisting of prokaryotic hosts and eukaryotic hosts.

16. The host of claim 12, wherein said host is selected from the group consisting of prokaryotic hosts and eukaryotic hosts.

* * * * *